(12) United States Patent
Humayun et al.

(10) Patent No.: US 9,999,542 B2
(45) Date of Patent: Jun. 19, 2018

(54) SYSTEMS, METHODS, AND DEVICES FOR CANNULA INSERTION

(71) Applicant: Doheny Eye Institute, Los Angeles, CA (US)

(72) Inventors: Mark Humayun, Glendale, CA (US); Jaw-Chyng Lormen Lue, San Gabriel, CA (US)

(73) Assignee: DOHENY EYE INSTITUTE, Los Angeles, CA (US)

( * ) Notice: Subject to any disclaimer, the term of this patent is extended or adjusted under 35 U.S.C. 154(b) by 309 days.

(21) Appl. No.: 14/793,980

(22) Filed: Jul. 8, 2015

(65) Prior Publication Data

US 2016/0015563 A1    Jan. 21, 2016

Related U.S. Application Data

(60) Provisional application No. 62/025,385, filed on Jul. 16, 2014.

(51) Int. Cl.
*A61F 11/00* (2006.01)
*A61F 9/007* (2006.01)
*A61B 17/34* (2006.01)

(52) U.S. Cl.
CPC ...... *A61F 9/00736* (2013.01); *A61B 17/3403* (2013.01); *A61B 17/3421* (2013.01); *A61F 9/007* (2013.01); *A61B 2017/3409* (2013.01)

(58) Field of Classification Search
CPC ............ A61B 17/3421; A61B 17/0218; A61B 17/3403; A61B 17/3415; A61B 17/3417; A61B 17/3468; A61B 2017/00362; A61B 2017/3405; A61B 2017/3409; A61F 9/00736; A61F 9/007
USPC .............................. 604/164.11; 606/108, 185
See application file for complete search history.

(56) References Cited

U.S. PATENT DOCUMENTS

| 3,509,883 | A | 5/1970 | Dibelius |
| 3,788,318 | A | 1/1974 | Kim et al. |
| 3,815,608 | A | 6/1974 | Spinosa et al. |
| 4,411,655 | A | 10/1983 | Schrek |
| 4,608,965 | A | 9/1986 | Anspach et al. |
| 4,899,729 | A | 2/1990 | Gill et al. |
| 5,053,009 | A | 10/1991 | Herzberg |

(Continued)

FOREIGN PATENT DOCUMENTS

| EP | 1 943 989 | 7/2008 |
| WO | WO 2001/052753 | 7/2001 |

(Continued)

OTHER PUBLICATIONS

International Preliminary Report on Patentability received from PCT Patent Application No. PCT/US2015/039682, dated Jan. 26, 2017; 7 pages.

(Continued)

*Primary Examiner* — Katherine M Shi
(74) *Attorney, Agent, or Firm* — Baker Botts L.L.P.

(57) ABSTRACT

A cannula insertion system configured to divide a cannula insertion process into a two-step process. The first step advances a needle portion a first distance and the second step advances the needle portion a second distance. The first step and the second step may be at different angles. At least one of the angles may be less than 90°. At least one of the steps may be mechanically assisted.

9 Claims, 25 Drawing Sheets

(56) References Cited

U.S. PATENT DOCUMENTS

| | | | |
|---|---|---|---|
| 5,139,511 | A | 8/1992 | Gill et al. |
| 5,156,160 | A * | 10/1992 | Bennett .............. A61B 10/0275 600/567 |
| 5,273,529 | A | 12/1993 | Idowu |
| 5,273,530 | A | 12/1993 | Del Cerro et al. |
| 5,312,417 | A | 5/1994 | Wilk |
| 5,334,164 | A | 8/1994 | Guy et al. |
| 5,400,770 | A | 3/1995 | Nakao et al. |
| 5,431,676 | A | 7/1995 | Dubrul et al. |
| 5,460,170 | A | 10/1995 | Hammerslag |
| 5,674,240 | A | 10/1997 | Bonutti et al. |
| 5,795,289 | A | 8/1998 | Wyttenbach |
| 5,800,394 | A | 9/1998 | Yoon et al. |
| 5,817,120 | A | 10/1998 | Rassman |
| 5,944,691 | A | 8/1999 | Querns et al. |
| 5,957,832 | A | 9/1999 | Taylor et al. |
| 5,957,902 | A | 9/1999 | Teves |
| 6,033,426 | A | 3/2000 | Kaji |
| 6,171,324 | B1 | 1/2001 | Cote et al. |
| 6,183,493 | B1 | 2/2001 | Zammit |
| 6,238,370 | B1 | 5/2001 | Neuhann et al. |
| 6,371,968 | B1 | 4/2002 | Kogasaka et al. |
| 6,398,803 | B1 | 6/2002 | Layne et al. |
| 6,454,783 | B1 | 9/2002 | Piskun |
| 7,100,612 | B2 | 9/2006 | Dunlap |
| 7,163,510 | B2 | 1/2007 | Kahle et al. |
| 7,297,106 | B2 | 11/2007 | Yamada et al. |
| 7,449,011 | B2 | 11/2008 | Wenchell et al. |
| 7,967,776 | B2 | 6/2011 | von Segesser |
| 8,105,236 | B2 | 1/2012 | Malandain et al. |
| 2003/0199737 | A1 | 10/2003 | Deslauriers et al. |
| 2004/0087968 | A1 | 5/2004 | Core |
| 2004/0260327 | A1 | 12/2004 | Mueller, Jr. et al. |
| 2005/0059934 | A1 | 3/2005 | Wenchell et al. |
| 2005/0125003 | A1 * | 6/2005 | Pinchuk .............. A61F 9/00781 606/108 |
| 2005/0222576 | A1 | 10/2005 | Kick et al. |
| 2006/0041291 | A1 | 2/2006 | Buzawa |
| 2006/0089607 | A1 | 4/2006 | Chen |
| 2007/0106319 | A1 | 5/2007 | Au et al. |
| 2007/0149997 | A1 | 6/2007 | Muller |
| 2007/0225568 | A1 | 9/2007 | Colleran |
| 2008/0215078 | A1 | 9/2008 | Bennett |
| 2009/0131881 | A1 | 5/2009 | Frisella, Jr. |
| 2009/0177288 | A1 | 7/2009 | Wallsten |
| 2009/0270817 | A1 | 10/2009 | Moreno et al. |
| 2011/0054260 | A1 | 3/2011 | Albrecht et al. |
| 2011/0118552 | A1 | 5/2011 | Fischvogt |
| 2012/0172668 | A1 | 7/2012 | Kerns et al. |
| 2013/0053875 | A1 | 2/2013 | Scheller et al. |
| 2013/0178822 | A1 | 7/2013 | Hickingbotham et al. |
| 2013/0204092 | A1 | 8/2013 | Hannaford et al. |
| 2014/0039456 | A1 | 2/2014 | Lerner |
| 2014/0046299 | A1 | 2/2014 | Shelton, IV |
| 2014/0180013 | A1 | 6/2014 | Hanlon et al. |

FOREIGN PATENT DOCUMENTS

| | | |
|---|---|---|
| WO | WO 2010/064062 | 6/2010 |
| WO | 2013/148275 | 10/2013 |

OTHER PUBLICATIONS

Assi et al., "Reversed Self-Sealing Pars Plana Sclerotomies", *Retina, The Journal of Retinal and Vitreous Diseases*, 2000, vol. 20, No. 6, pp. 689-692.

Bhende et al., "Ultrasound Biomicroscopy of Sclerotomy Sites after Pars Plana Vitrectomy for Diabetic Vitreous Hemorrhage", *Ophthalmology*, Sep. 2000, vol. 107, No. 9, pp. 1729-1736.

Boker et al., "Ultrasound Biomicroscopy for Examination of the Sclerotomy Site After Pars Plana Vitrectomy", *American Journal of Ophthalmology*, Dec. 1994, vol. 118, No. 6, pp. 813-815.

Chen, "Sutureless Pars Plana Vitrectomy Through Self-sealing Sclerotomies", *Arch Ophthalmol.*, Oct. 1996, vol. 114, pp. 1273-1275.

Eckardt, "Transconjunctival Sutureless 23-Gauge Vitrectomy", *Retina, The Journal of Retinal and Vitreous Diseases*, 2005, vol. 25, No. 2, pp. 208-211.

Fine et al., "Outcomes of 77 Consecutive Cases of 23-Gauge Transconjunctival Vitrectomy Surgery for Posterior Segment Disease", *Ophthalmology*, Jun. 2007, vol. 114, No. 6, pp. 1197-1200.e3.

Fujii et al., "A New 25-gauge Instrument System for Transconjunctival Sutureless Vitrectomy Surgery", *Ophthalmology*, Oct. 2002, vol. 109, No. 10, pp. 1807-1812.

Hotta et al., "Examination of the Sclerotomy Site in Eyes With Proliferative Diabetic Retinopathy After Vitrectomy", *Retina, The Journal of Retinal and Vitreous Diseases*, 2000, vol. 20, No. 1, pp. 52-58.

Jackson, Modified Sutureless Sclerotomies in Pars Plana Vitrectomy, *American Journal of Ophthalmology*, Jan. 2000, vol. 129, No. 1, pp. 116-117.

Kwok et al., "Modified Sutureless Sclerotomies in Pars Plan Vitrectomy", *American Journal of Ophthalmology*, Jun. 1999, vol. 127, No. 6, pp. 731-733.

Kwok et al., "Ultrasound Biomicroscopy of Conventional and Sutureless Pars Plana Sclerotomies: A Comparative and Longitudinal Study", *American Journal of Ophthalmology*, Aug. 2001, vol. 132, No. 2, pp. 172-177.

Rahman et al., "Self-Sealing Sclerotomies for Sutureless Pars Plana Vitrectomy", *Ophthalmic Surg Lasers*, Dec. 2000, vol. 31, No. 6, pp. 462-466.

Schmidt et al., "Selbstschließende, nahtlose Sklerotomie zur Parsplana-Vitrektomie", *Klin Monatsbl Augenheilkd*, 1999, vol. 2115, pp. 247-251.

Extended European Search Report issued in European Patent Application No. 10819351.7, dated Apr. 2, 2013.

International Search Report and Written Opinion in PCT Application No. PCT/US2010/049722, dated Nov. 17, 2010.

International Preliminary Report on Patentability in PCT Application No. PCT/US2010/049722, dated Feb. 14, 2012.

Claus Eckardt, "Transconjunctival Sutureless 23-Gauge Vitrectomy," Retina, The Journal of Retinal and Vitreous Diseases, Brief Reports, vol. 25, No. 2; 4 pages, 2005.

International Search Report and Written Opinion, Application No. PCT/US2015/39682; 18 pages, dated Jan. 12, 2016.

Extended European Search Report for European Patent Application No. 15821364.5, dated Nov. 30, 2017; 8 pages.

* cited by examiner

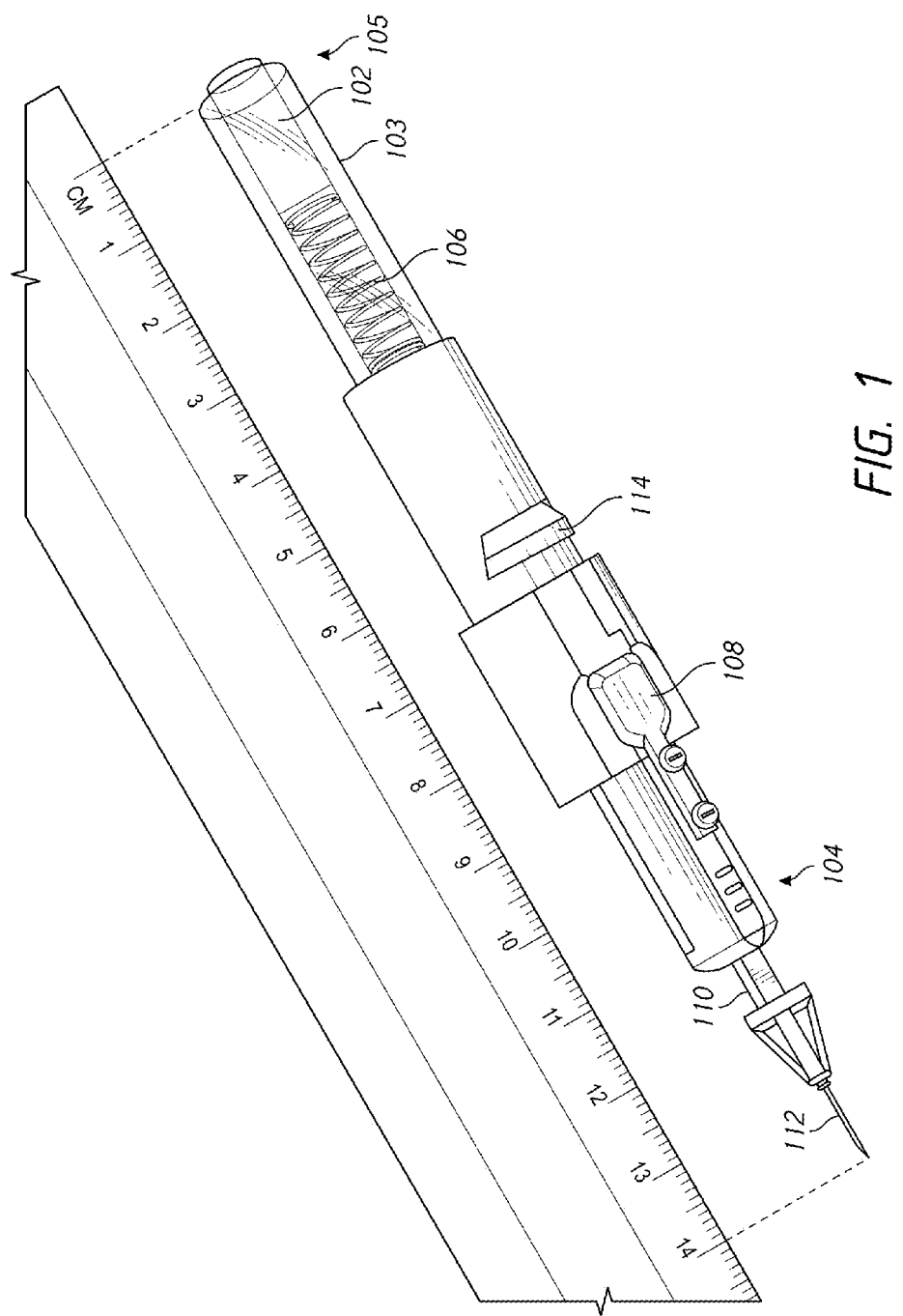

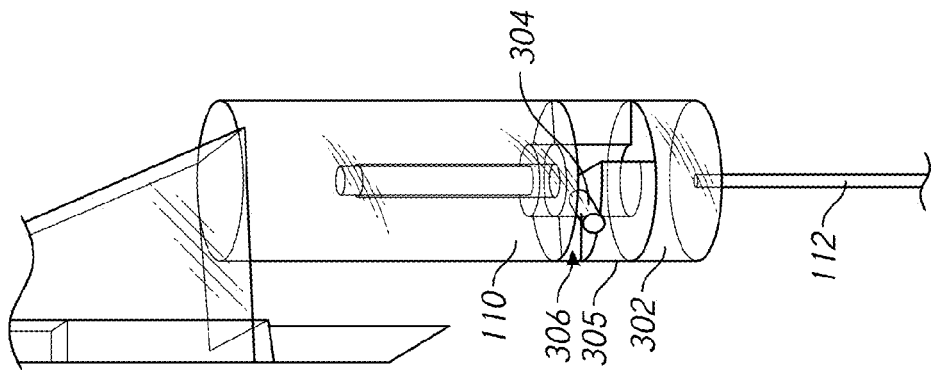
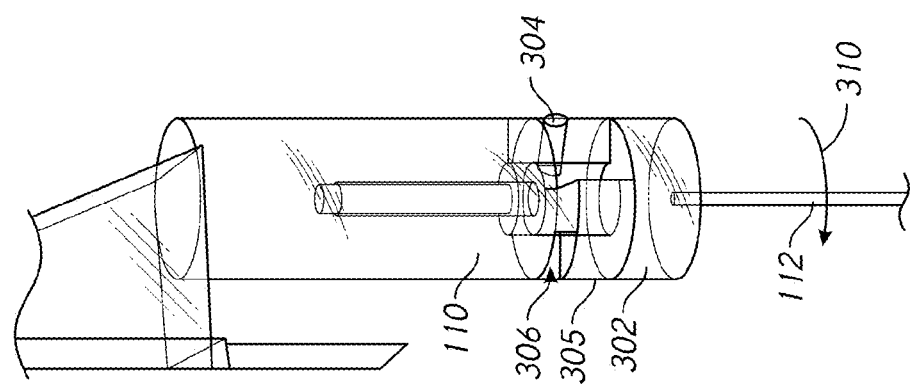
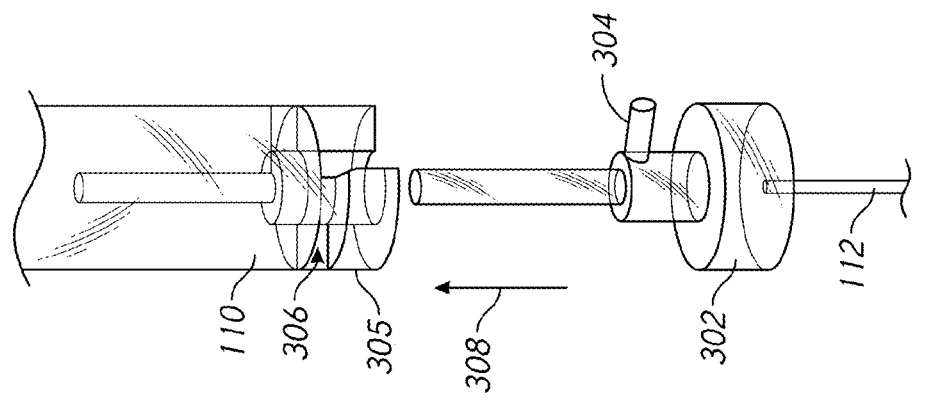

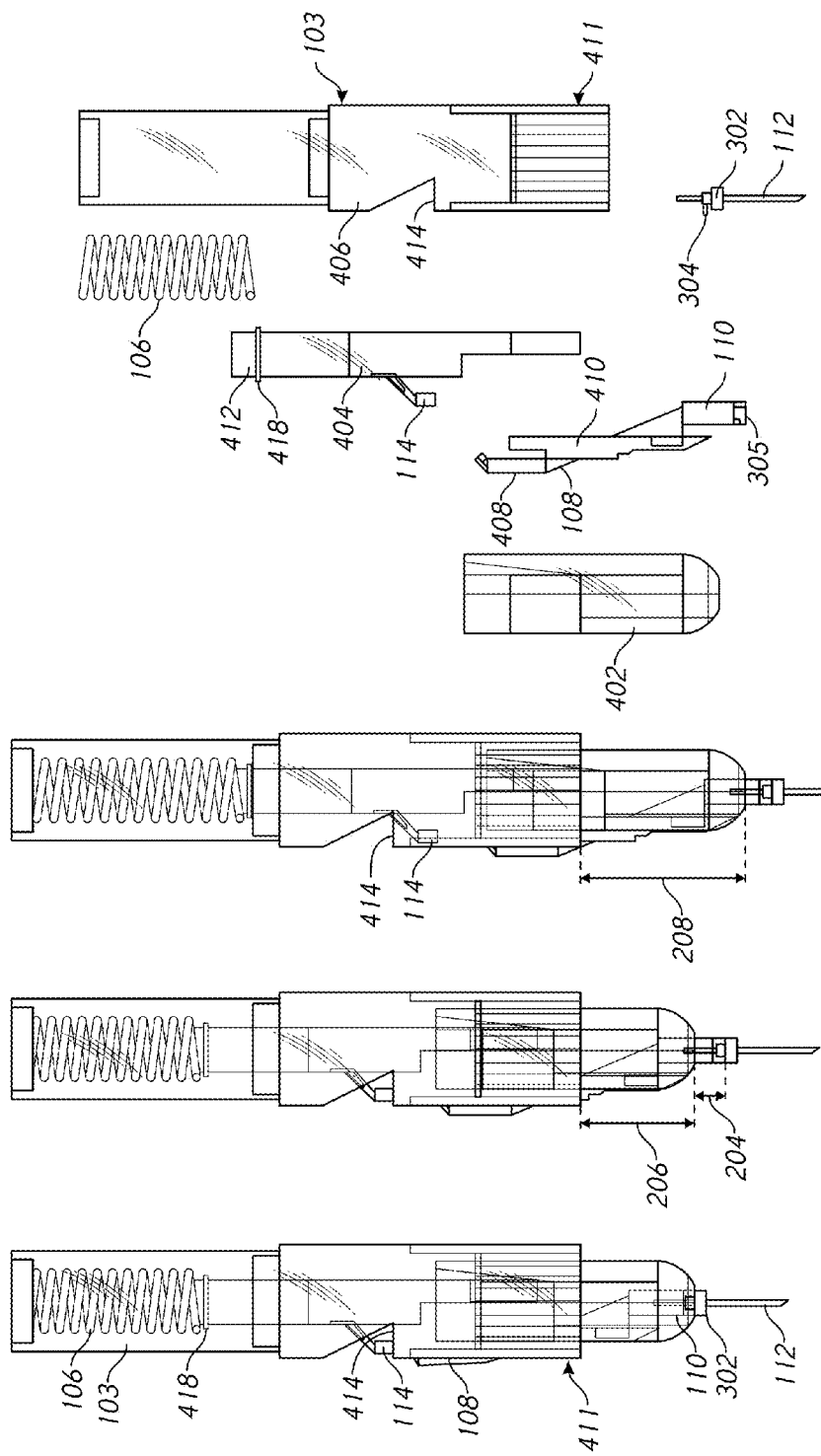

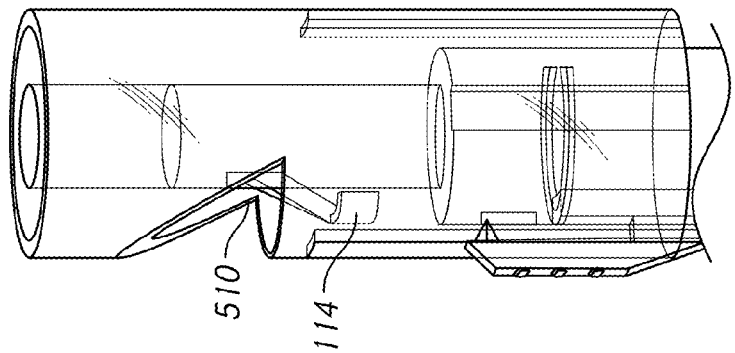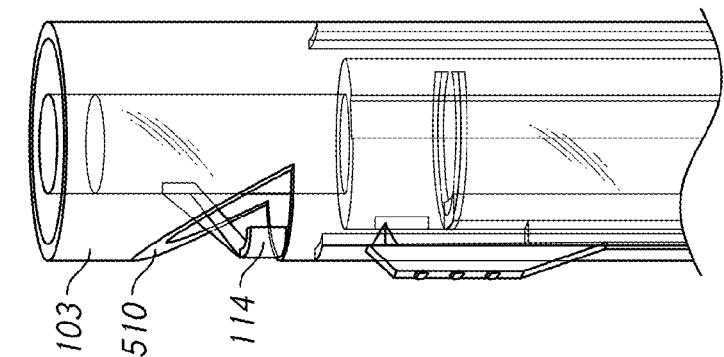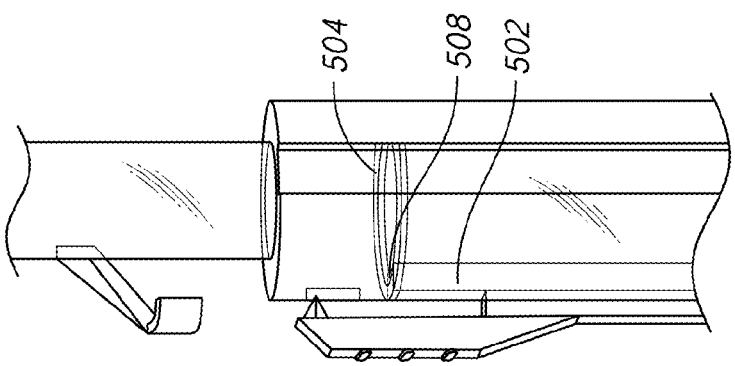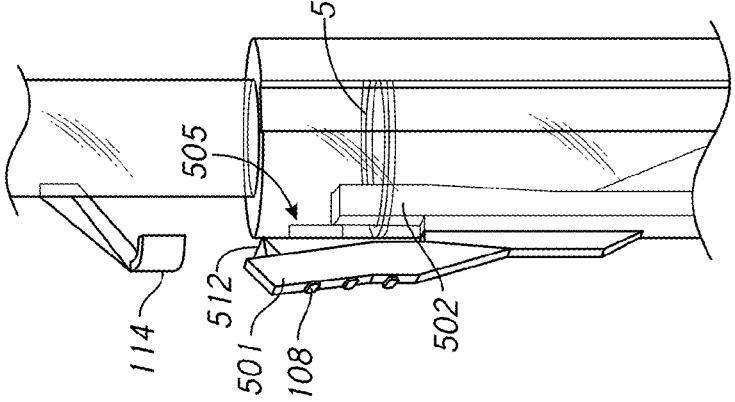

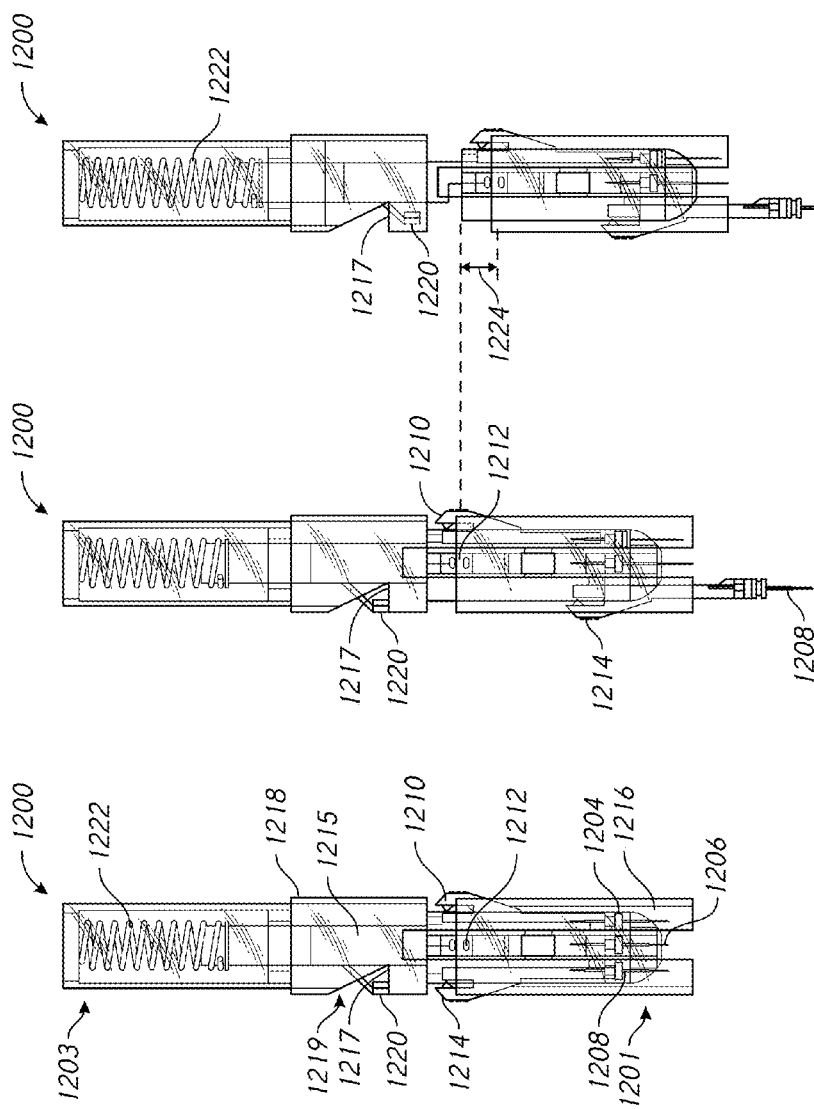

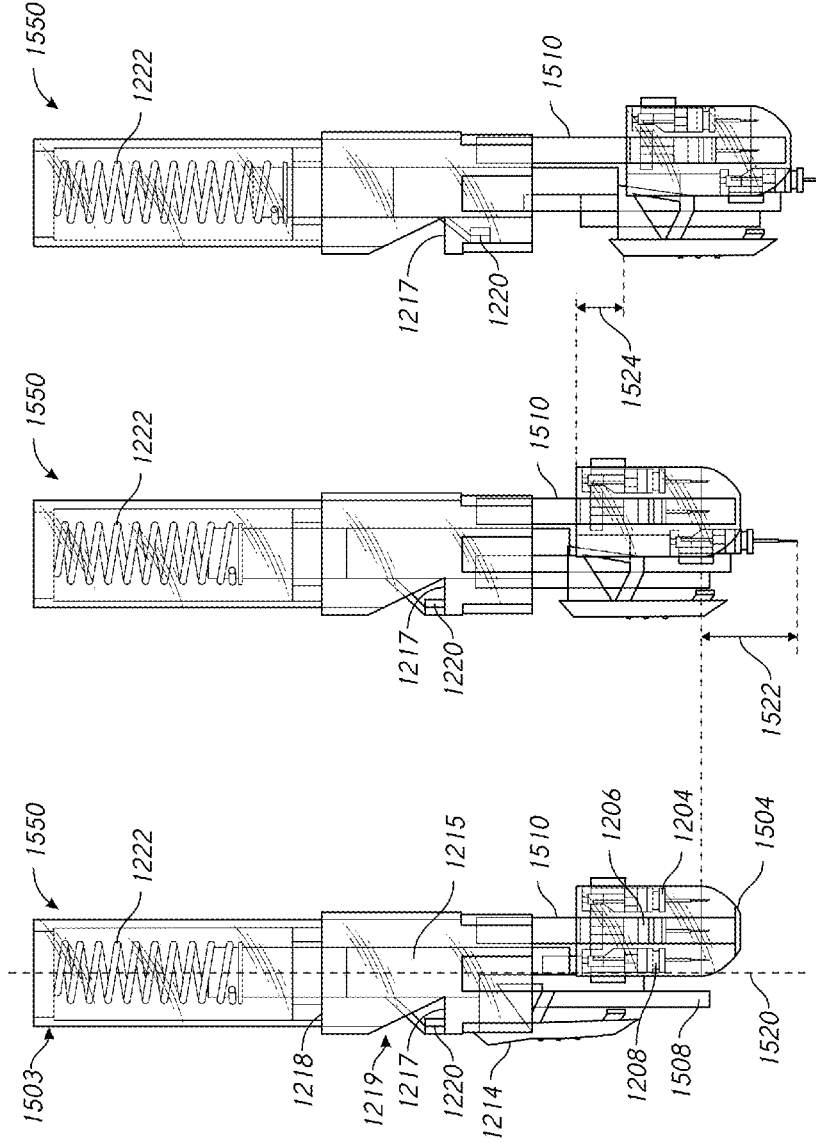

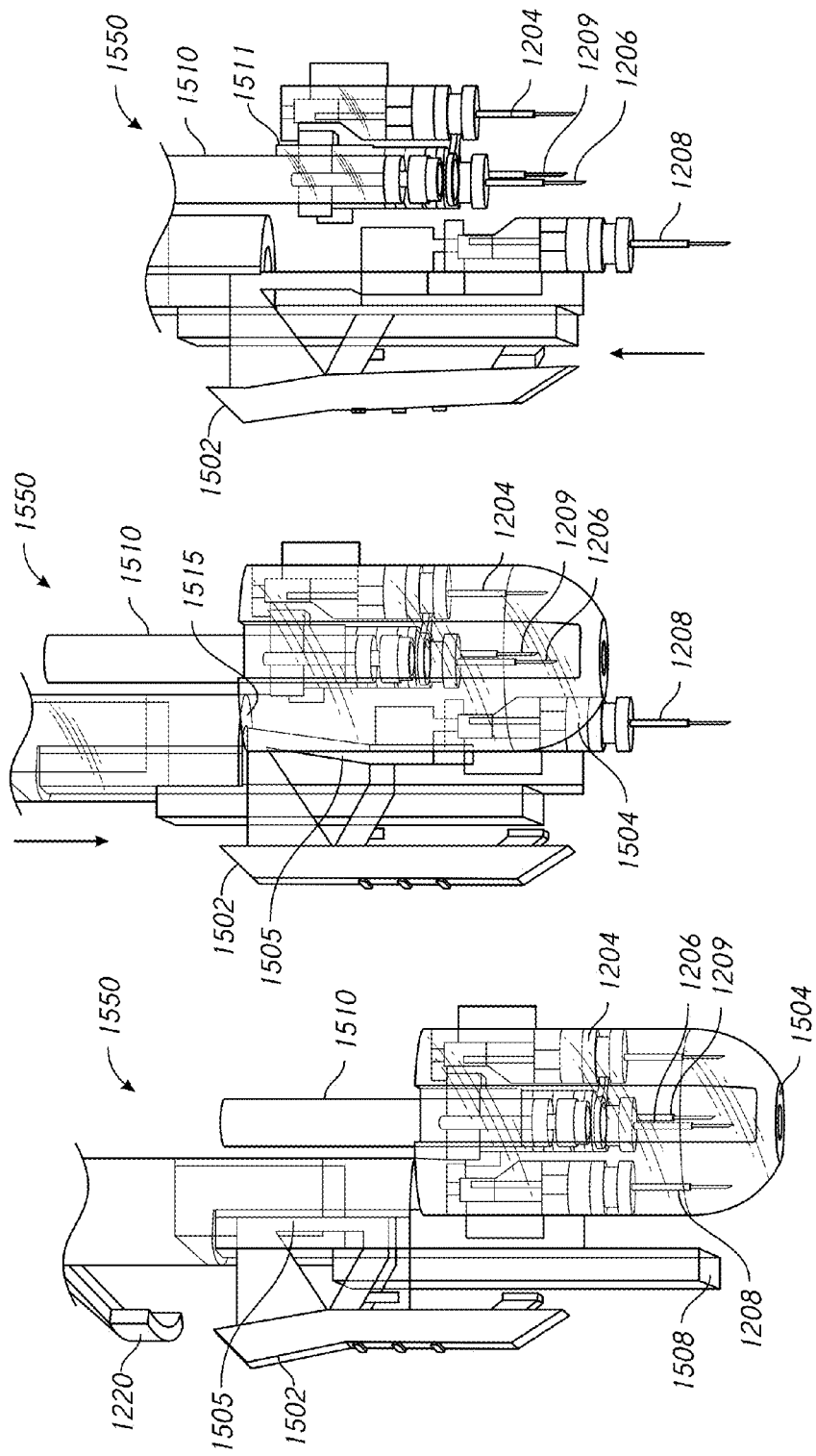

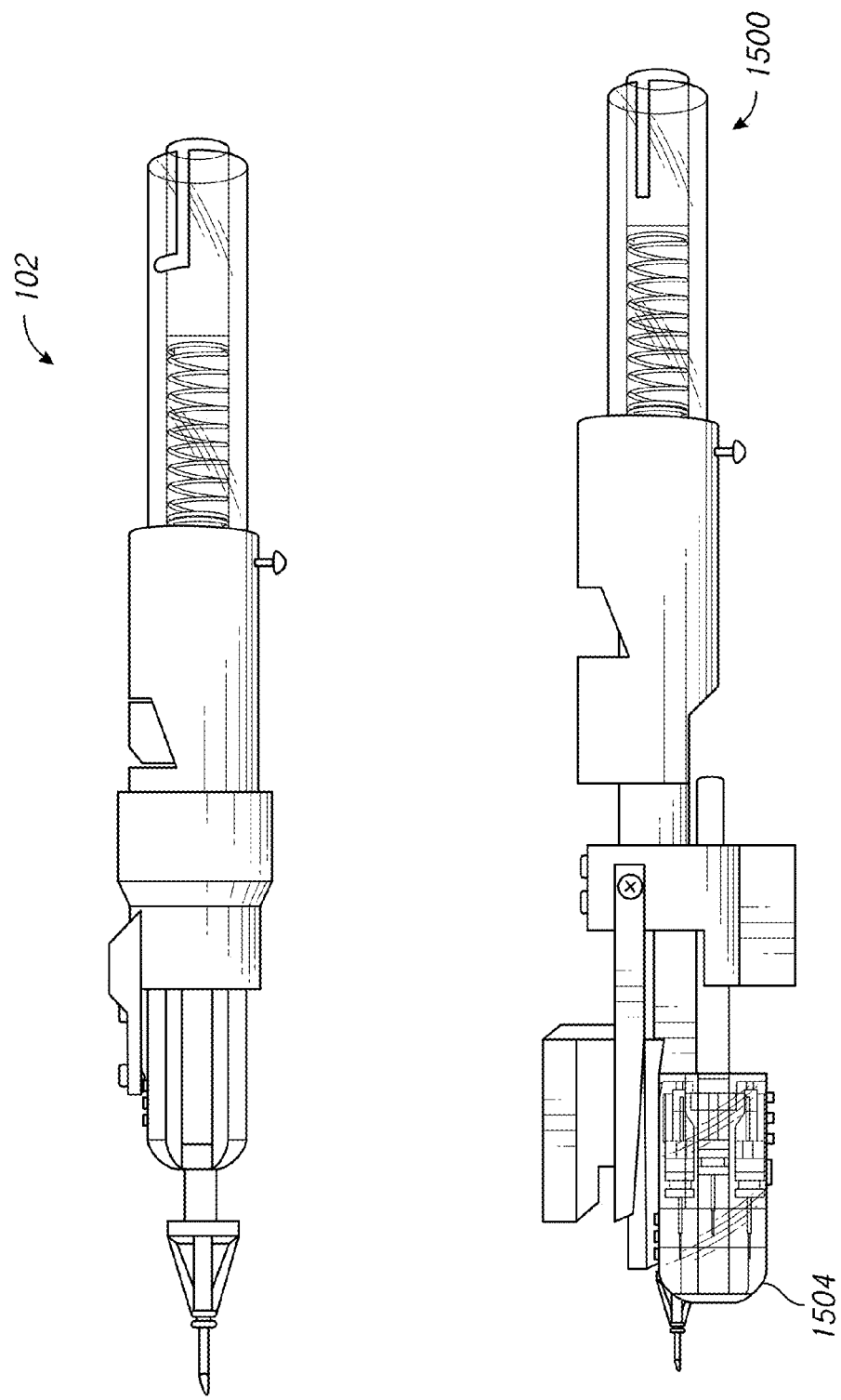

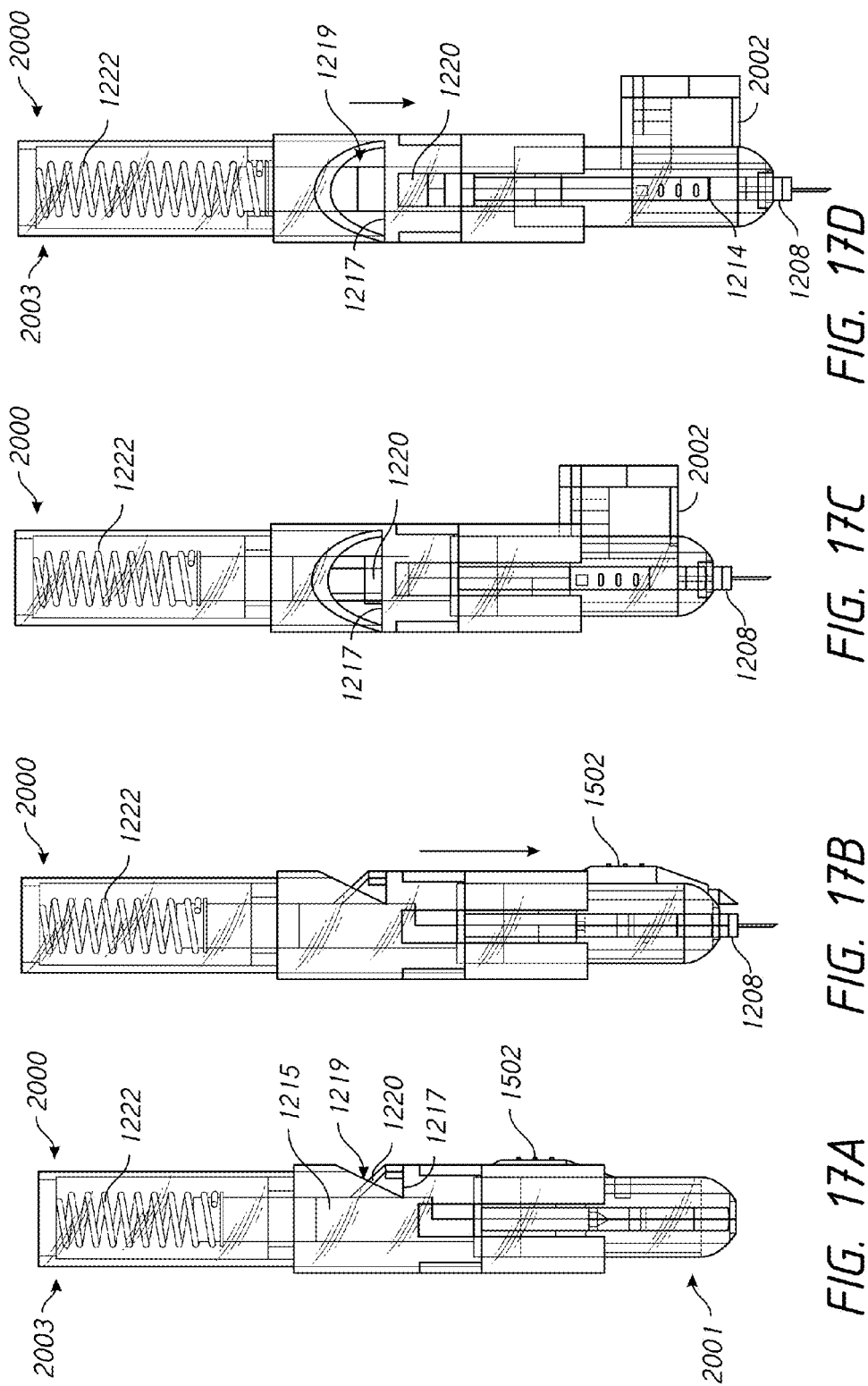

SYSTEMS, METHODS, AND DEVICES FOR CANNULA INSERTION

INCORPORATION BY REFERENCE TO ANY PRIORITY APPLICATIONS

The present application claims priority benefit of U.S. Provisional Patent App. No. 62/025,385, filed on Jul. 16, 2014. Any and all applications for which a foreign or domestic priority claim is identified in the Application Data Sheet as filed with the present application are hereby incorporated by reference under 37 C.F.R. § 1.57.

BACKGROUND

Field

The disclosure relates generally to the field of insertion systems, and more particularly to systems for cannula insertion.

Description of the Related Art

In ophthalmic surgery, and in other surgical contexts, a surgeon may desire to create a port opening on the surface tissue of a patient and to insert a cannula through which the surgeon can perform surgical operations. Generally, such port openings are called cannulas in the ophthalmic surgery context.

SUMMARY

In some embodiments, a method of implanting a cannula in an eye of a patient comprises, or alternatively consists essentially of, positioning a cannula insertion system at a first angle relative to a surface of the eye, distally advancing a trocar-cannula pair into the eye at the first angle, positioning the cannula insertion system at a second angle relative to the surface of the eye, and distally advancing the trocar-cannula pair further into the eye at the second angle. The trocar-cannula pair comprises a needle portion and a cannula.

The first angle may be less than 90°. The first angle may be 45°. The second angle may be 90°. Distally advancing the trocar-cannula pair into the eye at the first angle may comprise distally advancing a slide inserter. Distally advancing the trocar-cannula pair into the eye at the first angle may comprise pressing a flexible trigger button. Distally advancing the trocar-cannula pair further into the eye at the second angle may comprise pressing a flexible trigger button. Pressing a flexible trigger button may comprise allowing a spring to decompress. The method may further comprise retracting the needle portion of the trocar-cannula pair out of the eye. The method may further comprise positioning a second trocar-cannula pair for positioning in the eye of the patient. Positioning the second trocar-cannula pair may comprise rotating the second trocar-cannula pair. Rotating the second trocar-cannula pair may comprise rotating a guiding trail tube having a longitudinal axis aligned with a longitudinal axis of the cannula insertion system. Rotating the second trocar-cannula pair may comprise rotating a revolver chamber having a longitudinal axis radially offset from a longitudinal axis of the cannula insertion system. Positioning the second trocar-cannula pair may comprise horizontally advancing the second trocar-cannula pair transverse to a longitudinal axis of the cannula insertion system.

In some embodiments, a two-stage cannula insertion system comprises, or alternatively consist essentially of, a housing, a control mechanism slidably movable relative to the housing, a spring, an activation mechanism coupled to the spring, a shaft coupled to the spring, and a trocar-cannula pair coupled to the control mechanism. The shaft is releasably engagable with the control mechanism. The control mechanism is configured to move independently of the shaft when the shaft is disengaged with the control mechanism. The trocar-cannula pair comprises a needle portion and a cannula.

The control mechanism may be configured to advance the trocar-cannula pair during a first stage. The activation mechanism may be configured to advance the trocar-cannula pair during a second stage. The system may further comprise a mechanical assembly housing a plurality of trocar-cannula pairs including the trocar-cannula pair. The mechanical assembly may be configured to disengage the needle portion from the control mechanism after the first stage. The mechanical assembly may be configured to couple a second trocar-cannula pair with the control mechanism. The mechanical assembly may comprise a rotatable guiding trail tube having a longitudinal axis aligned with a longitudinal axis of the cannula insertion system. The mechanical assembly may comprise a rotatable revolver chamber having a longitudinal axis radially offset from a longitudinal axis of the cannula insertion system. The mechanical assembly may comprise a cartridge configured to horizontally advance the second trocar-cannula pair transverse to a longitudinal axis of the cannula insertion system.

In some embodiments, a two-stage cannula insertion system for use in ophthalmic surgery comprises, or alternatively consists essentially of, a first stage insertion mechanism and a second stage insertion mechanism. The first stage insertion mechanism is configured to insert a trocar-cannula pair partially into ocular tissue at a first angle. The trocar-cannula pair comprises a needle portion and a cannula. The second stage insertion mechanism is configured to insert the trocar-cannula pair through the ocular tissue at a second angle and to implant the cannula in the ocular tissue. The needle portion is removable while maintaining the cannula in the ocular tissue.

The system may further comprise a mechanical assembly housing a plurality of trocar-cannula pairs including the trocar-cannula pair. The first stage insertion mechanism may be configured to releasably engage at least one of the plurality of trocar-cannula pairs housed in the mechanical assembly. At least one of the first stage insertion mechanism and the second stage insertion mechanism may be configured to be automatically activated by a user engaging a button.

In some embodiments, a system comprises a two-stage inserter device for semi-automatically inserting a cannula into body tissue during a surgical operation, for example, for ophthalmic surgery. In some embodiments, the system comprises a housing. The system can comprise a first stage assembly. In some embodiments, the first stage assembly comprises a first inner locking shaft with attached deformable first cantilever structure that the said first cantilever structure can be pressed and deformed toward the center of the shaft. In some embodiments, the first cantilever can recover to its original shape if no force exerts on it. In some embodiments, the system comprises a first flexible activation button that the inner extrusion structure can push inward and cause the deformable cantilever to bend and/or deform toward the center of the shaft. In some embodiments, the system comprises a first outer locking shell that has an opening on the shell that can latch the cantilever structure along the longitudinal direction of the shell.

In some embodiments, the system comprises a first guide trail that is attached to the inside of the first outer locking shell, is able to guide the longitudinal slide motion of the inner locking shaft, and/or functions as a mechanical stop to inhibit or prevent the first cantilever from moving away from the latching position so the latching mechanism is secured. In some embodiments, the system comprises a first spring that can push the first inner locking shaft and first outer locking shell apart once released along the longitudinal direction of the spring. In some embodiments, the system comprises a second stage assembly. In some embodiments, the second stage assembly comprises a second inner locking shaft with attached deformable second cantilever structure that the second cantilever structure can be pressed and deformed toward the center of the shaft.

In some embodiments, the second cantilever can recover to its original shape if no force exerts on it. In some embodiments, the system comprises a second flexible activation button that the inner extrusion structure can push inward and cause the second deformable cantilever to bend and/or deform toward the center of shaft. In some embodiments, the system comprises a second outer locking shell that has an opening on the shell that can latch the cantilever structure along the longitudinal direction of the shell. In some embodiments, the system comprises a second guide trail that is attached to the inside of the first outer locking shell. In some embodiments, the second guide is able to guide the longitudinal slide motion of the inner locking shaft, and can function as a mechanical stop to inhibit or prevent the first cantilever from moving away from the latching position so the latching mechanism is secured.

In some embodiments, the system comprises a second spring that can push the first inner locking shaft and first outer locking shell apart once released along the longitudinal direction of the spring. In some embodiments, the system comprises an off-axis mechanical hollow interlock structure close to the end of the inner locking shaft for interlocking with a trocar or trocar agent at the shaft's distal end; has an off-axis concave hollow channel and a connected hollow bay structure that allows the external interlock structure to engage, move in and then stay in the bay securely. In some embodiments, the system comprises a trocar or a trocar agent that has a sideway extruded beam functioning as an off-axis mechanical interlock for interlocking the hollow interlock structure on the shaft.

In some embodiments, the system comprises a cannula that is loaded on but separable from the trocar or trocar agent. In some embodiments, the second spring comprises a greater force constant than the first spring. In some embodiments, the force and momentum generated from the second spring once its energy is released are greater than those from the second spring. In the first stage, in some embodiments, one end of the first spring exerts force on part of the first inner locking shaft and the other end of the first spring exerts force on part of the first outer locking shell. In some embodiments, the first locking shaft is attached to the second outer shell.

In the second stage, In some embodiments, one end of the second spring exerts force on part of the second inner locking shaft and the other end of the second spring exerts force on part of the second outer locking shell. In some embodiments, the two springs can be replaced by mechanical structures or mechanisms that can store potential energy and release later upon activation. The mechanisms for storing potential energy or driving the shaft can comprise rubber band with pulley, pneumatic pump, electromagnetic transducer, linear motor, pneumatic piston, or the like. In some embodiments, the relative locations of the two stage assemblies are stacked along their longitudinal direction. In some embodiments, one stage assembly is hollow in center to accommodate/enclose the other stage assembly in a concentric fashion. In some embodiments, the one stage assembly can be moving parallel to the moving direction of the other stage assembly in an off-axis parallel motion direction fashion.

In some embodiments, the system comprises a two-stage inserter device for semi-automatically inserting a cannula into a body during, for example, an ophthalmic surgical procedure. In some embodiments, the system comprises a housing and a first stage assembly. In some embodiments, the system comprises an h-shape slider inner shaft. The h-shape slider can comprise a right leg and left leg. In some embodiments, the right leg (beam) of the "h" shape is flexible and deformable when it is manually pressed at the beam's side and can recover when not pressed.

In some embodiments, the left leg (beam) of the h-slider is non-flexible. In some embodiments, the h-shape slider comprises a top beam. The top beam of the h-slider can be the main axial structure of the shaft and has protruded blocks at both sides (inward and outward from paper when reading "h") for guiding the sliding motion in trails in later front house structure, and can comprise an off-axis mechanical hollow interlock structure close to the distal end of the top beam of the h-slider for interlocking with a trocar or trocar agent. In some embodiments, the hollow interlock structure has an off-axis concave hollow channel and a connected hollow bay structure that allows the external interlock structure to engage, move in and then stay in the bay securely.

In some embodiments, the system comprises a trocar or a trocar agent that has a sideway extruded beam functioning as an off-axis mechanical interlock for interlocking the hollow interlock structure on the h-slider. In some embodiments, the system comprises a front house shell that has an elongate side opening functioning as a guide trail for the h-slider.

In some embodiments, one of the inner surface end of the elongated side opening can stop and latch the terminal face of the non-flexible left beam of the h-slider from moving backward. In some embodiments, the system comprises two elongate grooves functioning as guide trails on both elongated inner side surfaces of the opening, to house the protruded blocks on top beam of the h-slider; has openings at both distal ends to allow the top beam (main shaft) of the h-slider to move through along the longitudinal direction of the shell; is mechanically connected and fixed with the later inner locking shaft.

In some embodiments, the system comprises a second stage assembly. In some embodiments, the second stage assembly comprises an inner locking shaft with deformable cantilever structure. In some embodiments, the cantilever structure can be pressed and deformed toward the center of the shaft. In some embodiments, the cantilever can recover to its original shape if no forces exerts on it; has a ring extrusion on the shaft functioning as a mechanical stopper against the later ring blocker in the outer locking shall, and can be mechanically connected and fixed with the front house. In some embodiments, the system comprises a flexible activation button that the inner extrusion structure can push inward and cause the deformable cantilever to bend and/or deform toward the center of shaft.

In some embodiments, the system comprises an outer locking shell that has an opening on the shell that can latch the cantilever structure along the longitudinal direction of the shell. In some embodiments, the system comprises a ring blocker structure protruded inward for stopping the longitudinal slide motion of the inner locking shaft. The ring blocker can function as a mechanical stop to inhibit or prevent the inner shaft from moving forward too far. In some embodiments, the system comprises a spring stopper at its distal end to allow the spring stay and exert force against this shell. In some embodiments, the system comprises a spring that can push the inner locking shaft and first outer locking shell apart once released along the longitudinal direction of the spring. In some embodiments, the system comprises a cannula that is loaded on but separable from the trocar or trocar agent.

In some embodiments, the system comprises a plurality of preloaded trocar-cannula pairs with each pair having an individual slider inserter surrounding the handpiece. The system can comprise a plurality of trocars and/or trocar agents. In some embodiments, each trocar and/or trocar agent can load a cannula. In some embodiments, each trocar and/or trocar agent comprises a sideway extruded beam that can function as an off axis mechanical interlock for interlocking a hollow interlock structure in an h-slide inserter.

In some embodiments, the system comprises a revolver chamber that comprises a plurality of trocar-cannula pairs. In some embodiments, the revolver chamber is configured to comprise only a single slide inserter. In some embodiments, the revolver chamber can be configured to comprise a plurality of slide inserters for each trocar-cannula pair. The revolver chamber can comprise a cylindrical housing configured to house a plurality of guiding trails. The revolver chamber can be configured to rotate with respect to a longitudinal axis of the revolver chamber. In some embodiments, the guiding trails comprises two grooves that can accommodate the side protrusion blocks of a trocar carrier that is configured to be loaded with a trocar-cannula pair. In some embodiments, the guiding trail can be configured to guide the sliding action of the trocar carrier in order to implant a trocar-cannula pair into a patient. In some embodiments, the system comprises a blocker structure at a center portion of the revolver chamber. The blocker structure can comprise a blocker disc structure that can latch to a protruded bottom block of the trocar carrier. In some embodiments, the blocker structure can be configured to inhibit or prevent trocar carriers that are not being used from sliding forward. In some embodiments, the system comprises a blocker disc structure that can be configured to latch onto the cannulas. In some embodiments, the blocker disc structure can inhibit or prevent the cannulas that are not in use from sliding forward.

In some embodiments, the system comprises a side cartridge configured to house a plurality of trocar-cannula pairs. The side cartridge comprises a single slide inserter configured to be loaded with a trocar-cannula pair from the side cartridge. In some embodiments, the side cartridge can be configured to be loaded with a plurality of trocar-cannula pairs with each having a slide inserter. In some embodiments, the side cartridge comprises a rectangular internal chamber that can be configured to house a plurality of trocar-cannula pairs. In some embodiments, the trocar-cannula pairs are rectangular. In some embodiments, the side cartridge comprises an internal pusher block that can be configured to push trocar-cannula pairs sideways towards the center of a cylindrical housing of the cannula insertion system. In some embodiments, the pusher block can be configured to be pushed by compressing a spring that is positioned between the internal end wall of the side cartridge and the internal side wall of the pusher block. In some embodiments, the spring can be substituted with a variety of drive mechanisms including but not limited to a rubber band and pulley apparatus, electromagnetic transducer, pneumatic pump, linear motor, pneumatic piston, or the like. In some embodiments, the slide inserter as disclosed in any of the embodiments herein can be powered by any of the foregoing drive mechanisms such that the slide inserter is configured to automatically insert partially the trocar needle into the sclera.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other possible features, aspects, and advantages of the embodiments of the invention are described in detail below with reference to the drawings of various embodiments, which are intended to illustrate and not to limit the embodiments of the invention. The drawings comprise the following figures in which:

FIG. 1 is a perspective view of an example cannula insertion system.

FIGS. 4A-4C illustrate example operations of an example trocar agent for coupling to a cannula insertion system.

FIGS. 5A-5C illustrate example operations of an example cannula insertion system.

FIG. 5D is an exploded view of the cannula insertion system of FIGS. 5A-5C.

FIGS. 6A-6D illustrate example operations of example control mechanisms for a cannula insertion system.

FIGS. 13A-13C illustrate an example cannula insertion system at different stages.

FIGS. 15F-15H illustrate an example cannula insertion system at different stages.

FIGS. 15I-15K further illustrate example operations of the cannula insertion system of FIGS. 15F-15H.

FIG. 16 juxtaposes the cannula insertion system of FIGS. 15A-15C and the cannula insertion system of FIG. 1.

FIGS. 17A-17D illustrate an example cannula insertion system.

DETAILED DESCRIPTION

Figure 2A:
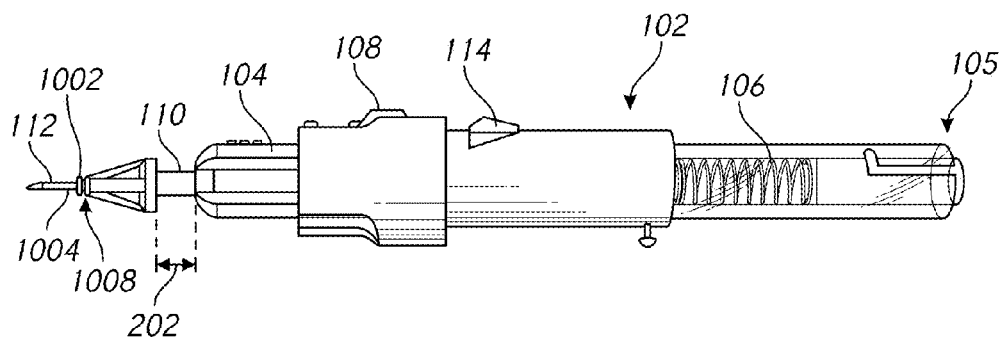
FIGS. 2A-2C depict an example of operating an example cannula insertion system.

Although several embodiments, examples, and illustrations are disclosed herein, it will be understood by those of ordinary skill in the art that the inventions described herein extends beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise combinations of features, and no single feature may be solely responsible for desirable attributes or essential to practicing the inventions herein described.

In ophthalmic surgery, and in other surgical operations, surgeons often insert cannulas into surgical openings, which are also known as sclerotomies in the ophthalmic surgical context. A cannula can comprise a cannula body and a cannula tube. The cannula body can be used to hold the cannula fixed in the surface tissue, for example, in the sclera. Generally, the cannula body is coupled to the cannula tube. The cannula tube can be a flexible tube that is inserted in the body to allow and guide surgical instruments into the interior body portion of a patient. In many instances, the cannula is inserted into the body manually by a surgeon using a handheld tool, which can comprise a needle and a handle portion. A cannula may be placed on the needle, and the surgeon, holding the handle portion, can insert the needle into the sclera and push the needle into the eye until the cannula is positioned to the sclerotomy. The surgeon is free to maneuver the handle portion in any manner the surgeon chooses. Use of such handheld tools can allow for great variation in the way cannulas are inserted into a sclera.

There is a need for the cannula insertion systems disclosed herein, which can allow for a consistent procedure for creating a sclerotomy. In some embodiments, the cannula insertion system can be configured to perform a large part of the task in creating a sclerotomy. For example, the cannula insertion system can be configured to insert a needle in the sclera with a consistent force. In some embodiments, the cannula insertion system can be configured to divide the cannula insertion process into a two-step process for the user (e.g., surgeon), which can improve procedure performance consistency. In some embodiments, the cannula insertion system is configured to be a low-cost device to manufacture and produce. The cannula insertion system can be a disposable device.

In some embodiments, the cannula insertion system is ergonomically designed to fit in a user's hand. The cannula insertion system can be configured to be operated with a single hand, thereby freeing the other hand of the user to perform other surgical tasks. In some embodiments, the cannula insertion system can be semi-automatic or fully automatic such that a user need not exert force on the body tissue in order to insert a cannula. By reducing the amount of user force, the surgical procedure can be less tiring for the user. Semi-automatic and fully automatic systems can ensure that a consistent amount of force is being exerted on the body tissue, which can inhibit or prevent injury and unintended damage to the body tissue. Semi-automatic and fully automatic systems can reduce the duration for a user to insert a cannula.

In some embodiments, the cannula insertion system can be configured with a two-stage insertion function, which may provide one or more of the advantages described herein. For example, the first stage of the insertion function can comprise a sliding step and the second stage of the insertion function can comprise an automatic mechanical releasing step. In some embodiments, the cannula insertion system can comprise a sliding portion to allow a user to manually slide the sliding portion from a proximal first position to a distal second position. By moving the sliding portion from the first position to the second position, the user can insert a needle portion that is coupled to the sliding portion into the sclera portion of an eye, for example at an angle less than 90°. In some embodiments, the needle portion is inserted only partially into the sclera and not entirely through the sclera during the first stage of the insertion function. In some embodiments, the user, during the first stage of the insertion function, can position the cannula insertion device at about a 45° angle relative to the surface of the sclera when manually sliding the sliding portion toward the sclera to insert the needle portion into the eye.

By angling the cannula insertion device at about a 45° angle, the user can create an oblique sclerotomy. The first stage may consistently create an oblique sclerotomy partially, at least partially, or fully thorough the sclera. After creating the oblique sclerotomy, the user can perform the second stage of the insertion function. During the second stage, the user can move the cannula insertion device from the about 45° angle to about a 90° angle relative to the surface of the sclera. After repositioning the cannula insertion device in about a 90° angle, the user can activate/trigger an automatic activation mechanism configured to allow a force to be applied to the needle portion in order to fully insert the needle portion through the sclera and into the vitreous. In applying the force on the needle portion, a cannula that is positioned on the needle portion is forced through the sclerotomy and is positioned on the sclera.

In some embodiments, during the first stage, only the needle or trocar enters the eye such that the insertion force is the force on the needle to create a portion of the aperture. In some embodiments, during the second stage, along with creating an additional portion of the aperture, a cannula that is larger than the needle is forced into the aperture such that the insertion force in the second stage is greater than the force on the needle to create the additional portion of the aperture. If the second stage is fully manual (e.g., without assistance by a device such as a spring), the application of manual force by a user may primarily push the eye towards the back of the socket, which can cause trauma and/or create a leaky incision.

In some embodiments, the application of the force positions the cannula in the vitreous of the eye and the cannula body in the sclera. The creation of the oblique sclerotomy in the first stage allows for the creation of a shearing force or a tension force up by the sclera on the cannula body. The creation of these forces may advantageously allow the cannula body to be more securely held in the sclera.

The forces are created at least partially by the creation of the oblique sclerotomy. The creation of the oblique sclerotomy in the first stage is more advantageous than the creation of a non-oblique sclerotomy that is generally created when the needle portion is inserted into the sclera initially at about a 90° angle relative to the surface of the sclera. The shearing forces or the tension forces created by a non-oblique sclerotomy are less than the shearing forces or tension forces created by an oblique sclerotomy. An oblique sclerotomy can better secure the cannula body than a non-oblique sclerotomy.

In some embodiments, the cannula insertion systems disclosed herein may advantageously provide a two-stage inserter function. In the first stage, the system allows for partial insertion of the needle portion into the wound, and in the second stage the system allows for the needle portion to be forced through the entire depth of the tissue. This two-stage insertion action can allow for the creation of an oblique sclerotomy, or other surgical opening, that is better suited for securing a cannula body in the sclera. The oblique sclerotomy may be consistently created across many cannulization procedures, for example, because a user of the device does not have to precisely stop insertion of a trocar partially through the sclera, which is typically about 0.3 mm to about 1 mm thick, but may rely on mechanical assistance that inhibits or prevents further insertion during a first stage.

The creation of the oblique sclerotomy, or other surgical opening, allows for the creation of additional shearing forces or tension forces that are not present in non-oblique sclerotomies or other non-oblique surgical openings. The creation of an oblique sclerotomy can be advantageous because the insertion of the needle portion at about a 45° angle creates a shelf-like wound in which the two shelf portions can come together and overlap each other after the needle portion and the cannula have been removed from the wound, allowing for self-sealing of the wound without suturing. Lack of suturing can reduce irritation of the eye and complications that might result from such irritation.

By reducing or eliminating suturing of the wound, patient healing time and patient discomfort can be reduced after the surgery. One-step insertion systems generally cannot create an oblique sclerotomy or other surgical opening because the needle portion is generally inserted into the sclera at about a 90° angle, and such a process does not create any shelf-like wound with two planes that can come together and overlap each other.

In some embodiments, a cannula insertion system comprises a plurality of trocar-cannula pairs for easy and fast insertion into an eye of a patient. In some embodiments, the cannula insertion system comprises a plurality of trocar-cannula pairs each having an individual slide inserter. In some embodiments, the cannula insertion system comprises a revolver chamber that can be configured to house a plurality of trocar-cannula pairs with only one slide inserter. In some embodiments, the cannula insertion system comprises a side cartridge chamber configured to house a plurality of trocar-cannula pairs that can be loaded onto a single slide inserter of the cannula insertion system. In some embodiments, the cannula insertion system comprises other mechanical assemblies for housing and/or loading a plurality of trocar-cannula pairs onto the cannula insertion system.

In some embodiments, the cannula insertion system is configured to be a cost effective device for reliably delivering trocar and cannula systems to an eye of a patient. In some embodiments, the operational procedure comprises two stages of semi-automatic insertion motions and one manual disengaging operation. In some embodiments, the cannula insertion system is configured to drive the trocar into the sclera of an eye of a patient to create a small incision in the sclerotomy. In some embodiments, the cannula insertion system is configured to deliver the cannula to the eye of the patient by guiding the cannula along the trocar in order to secure the cannula to the sclerotomy securely. The cannula insertion system can be configured to disengage the trocar from the cannula manually. In some embodiments, the cannula is configured to be left in the sclerotomy of the eye of the patient to create a port for instruments to enter and exit the internal chamber of the eye. In some embodiments, the cannula insertion system is configured to insert trocar-cannula pairs with a two step action that is triggered by the user. In some embodiments, the cannula insertion system is configured to drive the trocar and the cannula forward when the user releases the loaded spring or other biasing mechanism in the cannula insertion system.

It can be advantageous to incorporate a plurality of trocar-cannula pairs into a cannula insertion system to reduce the surgical duration for loading trocar-cannula pairs individually onto a cannula insertion system. In some embodiments, it is advantageous for a plurality of trocar-cannula pairs to be preloaded onto a cannula insertion system to reduce or mitigate the risk of contamination due to loading trocar-cannulas individually. In some embodiments, the cannula insertion system is configured to occupy a smaller space and/or have a lower cost for storage and/or packaging. In some embodiments, the cannula insertion system is configured to create a sclerotomy wound consistently such that the size of the wound and the time for generating the sclerotomy can be about the same. In some embodiments, the cannula insertion system is configured to have a two stage action for insertion of the cannula-trocar to allow the user to perform consecutive incisions with two different angles. In some embodiments, the system is configured to create a first incision by introducing the trocar into a sclera by utilizing a 45° angle with respect to the surface of the sclera. In some embodiments, the system is configured to create a second incision to deliver the cannula at a 90° angle with respect to the surface of the sclera. In some embodiments, the foregoing two-step incision process can allow the cannula to be better secured in the sclera than a one-step incision process. In some embodiments, the second incision action is much stronger than the first incision action so that the cannula can be successfully delivered along the trocar-guided incision pathway. In some embodiments, the second incision can overcome resistance of the sclera around the sclerotomy because the outer diameter of the cannula tube on the trocar needle is greater than the outer diameter of the trocar guide needle, allowing use of greater force. In some embodiments, the cannula insertion system is a low cost and/or disposable device. In some embodiments, the cannula insertion system is configured to allow a user to only use the index finger of the user to trigger the two stage incision process.

FIG. 1 is a perspective view of an example cannula insertion system 102. In some embodiments, the cannula insertion system 102 comprises a substantially cylindrical device having a proximal end 105 and a distal end 104. At the distal end 104, the system can comprise a needle portion 112 configured to pierce tissue, for example the sclera of an eye. In some embodiments, the needle portion 112 comprises a 25 gauge needle configured to puncture through body tissue. One of ordinary skill in the art will appreciate that other gauge needles can be utilized for needle portion 112, for example 15 gauge, 20 gauge, 23 gauge, 27 gauge, 30 gauge, 35 gauge, or the like. In some embodiments, the needle portion 112 is coupled to a sliding portion 110. The sliding portion 110 can be configured to slide within a hollow tubular portion of the cannula insertion system 102. In some embodiments, the sliding portion 110 is coupled to a slider control mechanism 108.

In some embodiments, the control mechanism 108 is configured to slide along a groove or channel positioned on the outer surface of the distal end 104 of the cannula insertion system 102. By grasping the cannula insertion system 102 in the palm of a hand of a user, the device 102 can be grasped between the thumb and the remaining fingers of the user. For example, the device 102 can be grasped like a flashlight. In some embodiments, the user can utilize the index finger or thumb of the user to slide the slider control mechanism 108 from a first position toward the distal end 104 to a second position. By distally advancing the slider control mechanism 108 using the index finger or thumb of the user, the slider portion 110 and the needle portion 112 also move forward in a distal direction to allow the needle portion 112 to puncture body tissue, such as the sclera of an eye.

The device 102 can comprise an activation or actuation mechanism 114 that is configured to release a spring or biasing mechanism 106 that is housed in the hollow tubular portion 103 of the device 102. In some embodiments, the spring 106 is coupled at the proximal end 105 of the device 102. At the distal end of the spring 106, the spring 106 is coupled to a shaft 404 (not shown) that is housed within the hollow tubular portion 103 of the device 102. In some embodiments, the shaft 404 is coupled to the sliding portion 110. When the user activates/triggers the activation mechanism 114, the load or force of a compressed spring 106 is released and a force is applied by the spring 106 on the shaft 404, causing the shaft 404 to slide forward in a distal direction. The sliding of the shaft 404 causes the sliding portion 110 and the needle portion 112 to move forward in a distal direction, allowing the needle portion 112 to further pierce into body tissue, such as the sclera. FIG. 1 shows a ruler for an example scale, but other sizes of the device 102 are possible (e.g., based at least partially on gauge of the needle portion 112).

Figure 2B:
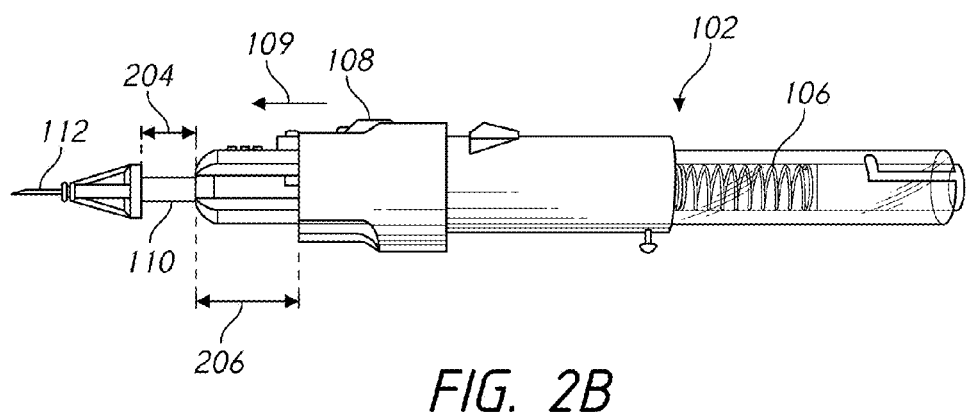
Figure 2C:
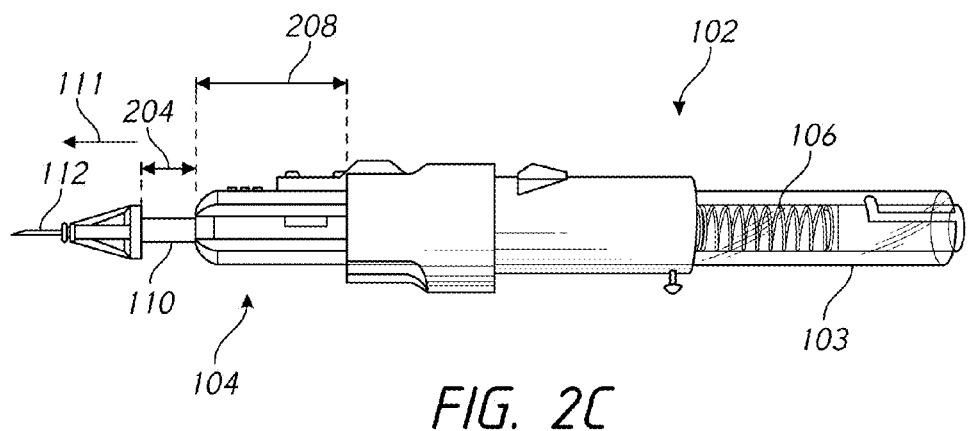

FIGS. 2A-2C depict an example of operating an example cannula insertion system 102. FIG. 2A shows the device 102 configured in a loaded configuration. In the loaded configuration, the device 102 comprises a cannula 1008 loaded on the needle portion 112. In some embodiments, the cannula 1008 comprises a cannula tube portion 1004 and/or a cannula body portion 1002. In some embodiments, as the needle portion 112 is pushed into the body tissue (e.g., by distal advancement of the sliding control mechanism 108), the cannula 1008 is also forced into the body tissue such that the cannula 1008 is secured and fixed in the body tissue by the cannula body portion 1002. In the loaded configuration, the spring 106 is in a compressed state in the hollow tubular portion 103 of the device 102.

FIG. 2B shows the device 102 after a first stage of a two-stage operation. In the first stage, a user can utilize slide or push the slider control mechanism 108 in a distal direction as indicated by the arrow 109 to move the slider portion 110 and the needle portion 112 forward in a distal direction. As shown in FIG. 2B, distal movement of the slider control mechanism 108 causes the slider portion 110 to move a distance illustrated by a post-first stage length 204. The length 204 is not substantially longer than the length 202 shown in FIG. 2A, which represents the visible length of the slider portion 110 prior to slider control mechanism 108 and the slider portion 110 being extended in a distal direction.

The length of translation of the slider control mechanism 108 may be the same or substantially the same as the length of translation of the slider portion 110, for example by direct mechanical engagement. In some embodiments, gears or other means may be used to increase or decrease the length of translation of the slider portion 110.

In some embodiments, the device 102 is configured to only extend the slider portion 110 a sufficient distance to enable the needle portion 112 to partially pierce, and not extend all the way through, the body tissue, such as the sclera. In the first stage, the user of the device 102 can position the needle portion 112 at about a 45° angle relative to the surface of the body tissue, such as the sclera. By positioning the needle portion 112 at about a 45° angle (or in some instances, at angle between about 89° and about 1°, between about 60° and about 30°, between about 50° and about 40°, and ranges therebetween), the user can slide the slider control mechanism 108 forward in a distal direction to allow the needle portion 112 to pierce the body tissue at an angle relative to the surface of the tissue, creating a shelf-like wound. The device 102 may be used for form a one or two angle oblique sclerotomy, which may provide one or more of the advantages described herein.

In some embodiments, a kit or package including the device 102 comprises an angle guide to help a user determine that the first stage insertion is at an angle or within a range of angles. The guide may help to stabilize the device 102 during advancement of the slider control mechanism 108 during the first stage.

FIG. 2C shows the device 102 after a second stage of a two-stage operation. A user can activate the second stage by using the index finger, for example, to activate or trigger the activation mechanism 114. In some embodiments, the spring 106 is maintained in a compressed state by the activation mechanism 114. By activating the activation mechanism 114, the compressed spring 106 that is housed in the hollow tubular portion 103 of the device 102 is released from the compressed state to an uncompressed state and applies a force that causes the sliding portion 110 and the needle portion 112 to advance further in the distal direction, as shown by the arrow 111. The additional movement forward in the distal direction causes the needle portion 112 to pierce entirely through the body tissue, such as the sclera.

By activating the activation mechanism 114, the slider portion 110 does not change length 204. Activating the activation mechanism 114 causes the distal portion 104 of the device 102 to extend from a length 206 (FIG. 2B) to a larger length 208 (FIG. 2C). The length 208 is substantially larger than the length 204, which can allow the needle portion to be extended through the body tissue, such as the sclera. In some embodiments, the user can position the device 102 at about a 90° angle relative to the surface of the body tissue prior to activating the activation mechanism 114. By moving the device 102 from a first angle (e.g., about 45°) to a second angle (e.g., about 90°), the cannula body portion 1002 can be securely positioned in the shelf-like wound between the angled edges.

Figure 3A:
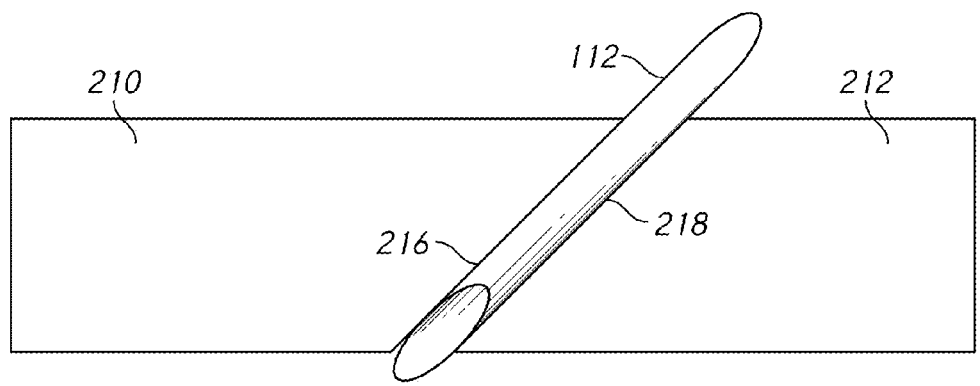
FIGS. 3A and 3B depict an example of creating a wound using an example cannula insertion system.
Figure 3B:
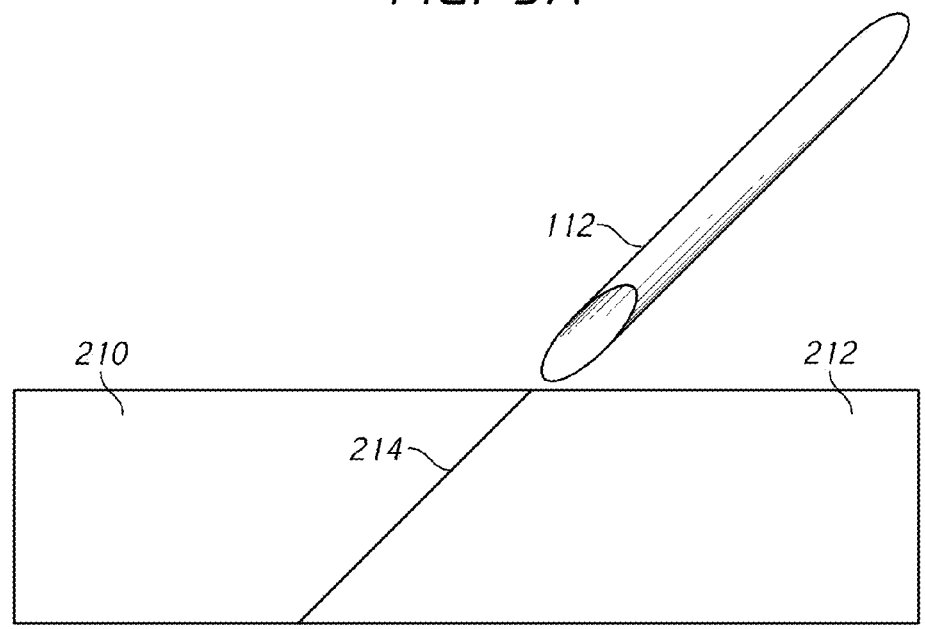

FIGS. 3A and 3B depict an example of creating a wound using an example cannula insertion system. The piercing of the body tissue at an angle can create a shelf-like wound in which the two planes 210, 212 of the wound appear similar to a shelf. Each plane 210, 212 comprises an angled edge 216, 218, respectively, of the wound. When the needle portion 112 of the cannula insertions system is removed from the wound 214, the angled edges 216, 218 can come together and overlap each other to form a self-sealing wound 214 that may not require sutures for closing the wound. FIGS. 3A and 3B schematically illustrate an oblique wound that can be created when the needle portion 112 pierces entirely through body tissue at an angle of about 45° relative to the surface of the body tissue. The angle may be steep enough that, in combination with the thickness of the tissue, a vertical line cannot pass through the wound 214 without modifying at least one of the edges 216, 218.

Figure 3C:
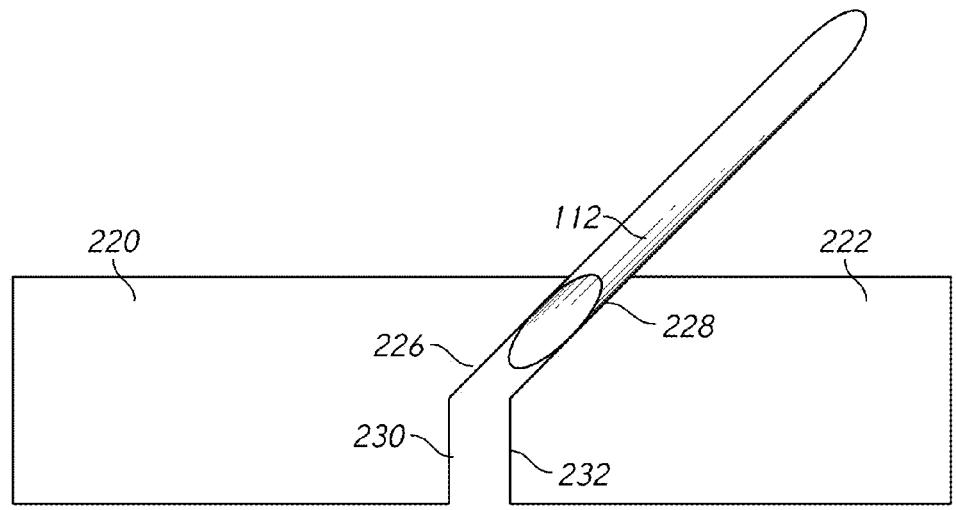
FIGS. 3C and 3D depict another example of creating a wound using an example cannula insertion system.
Figure 3D:
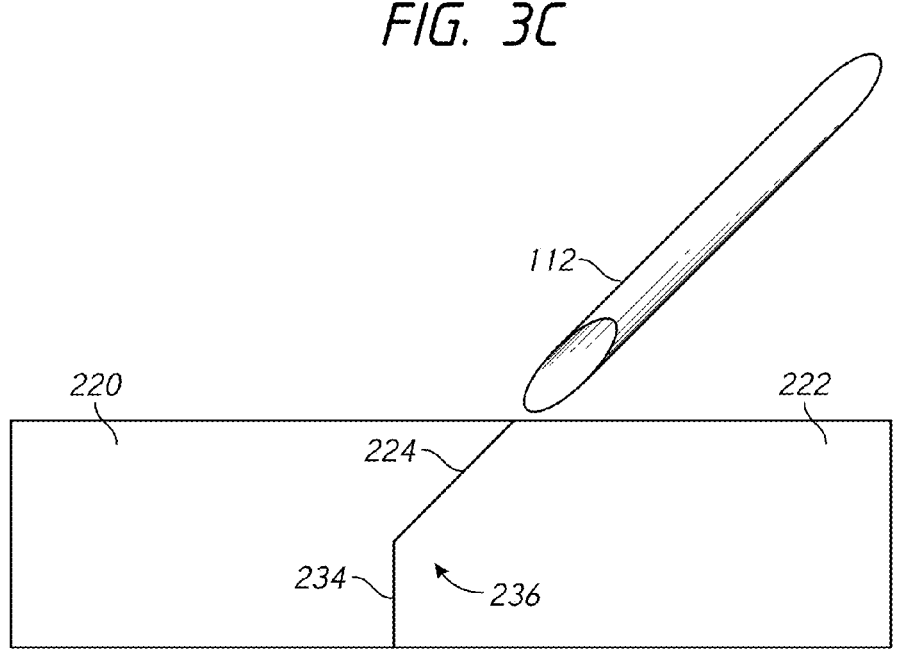

FIGS. 3C and 3D depict another example of creating a wound 236 using an example cannula insertion system. The wound 236 comprises an oblique portion 224 and a vertical portion 234 that can be created when, during a first stage of a cannula insertion process, a user partially pierces the body tissue with the needle portion 112 of a cannula insertion system at an angle of about 45° relative to the surface of the body tissue, and, during a second stage of the cannula insertion process, the user pierces entirely through the tissue at an angle of about 90° relative to the surface of the body tissue. The piercing of the body tissue in such a manner creates two planes 220, 222 that appear similar to a shelf. Each plane 220, 222 comprises an angled edge 226, 228, respectively, of the wound 236 as well as a vertical edge 230, 232, respectively. When the needle portion 112 is removed from the wound 236, the angled edges 226, 228 ad the vertical edges 230, 232 can come together and overlap each other to form a self-sealing wound 236 that may not require sutures for closing the wound 236. The angle of the first stage may be steep enough that, in combination with the thickness of the tissue, a vertical line cannot pass through the wound 236 without modifying at least one of the edges 226, 228.

In some embodiments, the wound 214 in FIGS. 3A and 3B and/or the wound 236 in FIGS. 3C and 3D can secure a cannula better than a wound with only a vertical portion that is created when a user pierces entirely through the body tissue at an angle of about 90° relative to the surface of the body tissue.

FIGS. 4A-4C illustrate example operations of an example trocar agent for coupling to a cannula insertion system. In some embodiments, the cannula insertion system (e.g., the system 102) comprises a coupling mechanism 305 at the distal end of the slider portion 110. In some embodiments, the coupling mechanism 305 comprises a groove 306. In some embodiments, the coupling mechanism 305 is configured to receive a trocar agent 302. By receiving a trocar agent 302, the system can be easily loaded with a needle portion 112. In some embodiments, the needle portion 112 is already loaded with a cannula 1008 (FIGS. 2A-2C). Loading a cannula 1008 on the needle portion 112 may advantageously allow the user to easily and quickly load a trocar agent 302 onto a cannula insertion system 102 by coupling the trocar agent 302 to the coupling mechanism 305.

To couple the trocar agent 302 to the coupling mechanism 305, a user can insert the trocar agent 302 into the coupling mechanism 305 until a protrusion 304 abuts a distal portion of the slider portion 110, as shown by the arrow 308 in FIG. 4A. To lock the trocar agent 302 into the coupling mechanism, the user can rotate the trocar agent 302 as shown by the arrow 310 in FIG. 4B whereby the protrusion 304 travels along the groove 306, for example until the protrusion 304 is locked into the groove portion 306 at a terminal end of the groove 306.

FIGS. 5A-5C illustrate example operations of an example cannula insertion system 500. FIG. 5D is an exploded view of the cannula insertion system 500 of FIGS. 5A-5C. In some embodiments, the slider control mechanism 108 can be implemented as a flexible h-slider with a front trocar agent locker. In some embodiments, the slider control mechanism 108 comprises a user interface portion 408 configured to allow the index finger, for example, of the user to interface with the slider control mechanism 108. In some embodiments, the slider control mechanism 108 comprises a linear center portion 410 that is coupled to the user interface portion 408 and that is configured to slide in a groove 412 on the distal end 411 of the hollow tubular portion 103.

In some embodiments, the slider control mechanism 108 comprises a slider portion 110 that is coupled to a linear center portion 410. In some embodiments, the user can interface with the user interface portion 408 to slide forward the slider control mechanism 108 to move the slider portion 110 forward, which pushes the needle portion 112 coupled to the slider portion 110 into body tissue. In some embodiments, the slider control mechanism 108 can move independently of a housing 402 and/or a shaft 404 to move or advance the needle portion 112 a distance 204. After moving the needle portion 112 the distance 204, in some embodiments, the slider control mechanism 108 is locked with the shaft 404 such that when the shaft 404 is advanced in a distal direction, the needle portion 112 coupled to the slider control mechanism 108 can advance in a distal direction with the shaft 404.

In some embodiments, the shaft 404 is positioned in the hollow tubular portion 103 of the device. A proximal end 416 of the shaft 404 can interact with the spring 106, for example abutting or coupled to the spring with a shoulder, lip, ring, or flange 418. In some embodiments, the spring 106 is housed in the hollow tubular portion 103 of the device 106. In some embodiments, the shaft 404 can be moved in a proximal direction to compress the spring 106. To lock the spring 106 in a compressed configuration, the proximal end of the hollow tubular portion 103 can be occluded (e.g., by a plug) and the activation mechanism 114 can be moved proximally to compress the spring 106 against the occlusion. The activation mechanism 114 is biased radially outwardly and, upon moving to at least the longitudinal position of a transverse surface 414 of the hollow tubular portion 103, can interface with (e.g., abut) the surface 414 (e.g., moving from the orientation of FIG. 5C to the orientation of FIG. 5B). The interfacing of activation mechanism 114 with the surface 414 inhibits or prevents the shaft 404 from advancing in a distal direction, thereby keeping the spring 106 in a compressed state and inhibiting or preventing the spring 106 from forcing the shaft 404 in a distal direction. FIGS. 5A and 5B show the activation mechanism 114 abutting the surface 414. As shown in FIG. 5B, distal movement of the slider control mechanism 108 causes the slider portion 110 to move a distance illustrated by a post-first stage length 204. In some embodiments, the length 204 is between about 0.3 mm and about 1 mm, between about 0.2 mm and about 0.5 mm, between about 0.1 mm and about 0.3 mm, or between about 0.1 mm and about 0.2 mm.

As shown in FIG. 5C, in some embodiments, the user can press the activation mechanism 114 radially inward to release the compressed spring 106. By depressing the activation mechanism 114 radially inward, the surface 414 no longer interfaces with the activation mechanism 114, which allows the shaft 404 to advance in a distal direction due to the decompression of the spring 106. As the spring 106 decompresses, the spring 106 exerts a force on the distal end of the shaft 404, which causes the shaft 404 to advance distally in the hollow tubular structure 103. By activating the activation mechanism 114, the slider portion does not change length 204. Activating the activation mechanism 114 causes the distal portion of the device to extend from a length 206 (FIG. 5B) to a larger length 208 (FIG. 5C).

In some embodiments, the difference between the length 206 and the length 208, which is the length that the needle portion 112 is further extended, is between about 0.3 mm and about 1 mm, between about 0.2 mm and about 0.8 mm, or between about 0.1 mm and about 0.5 mm. In some embodiments, the sum of the length 204 and the difference between the length 206 and the length 208 is between about 0.5 mm and about 1.5 mm, which would be sufficient to traverse a sclera having a thickness between about 0.3 mm and about 1 mm at a 45° angle. In some embodiments, a ratio between the length 204 and the difference between the length 206 and the length 208 is between about 1:1 and about 1:5, between about 1:1 and about 1:3, between about 1:1 and about 1:4, or between about 1:1 and about 1:2. Other lengths and ratios are also possible. For example, the length 204 may be configured to be more than half of the thickness of the sclera.

FIG. 5D shows the hollow tubular portion 103, the spring 106, the slider control mechanism 108, the trocar mechanism 302, the housing 402, and the shaft 404 in exploded view. Other elements and/or modifications thereof may be used instead of and/or in combination with the illustrated elements.

FIGS. 6A-6D illustrate example operations of example control mechanisms for a cannula insertion system 500. The system 500 may be used for form a one or two angle oblique sclerotomy, which may provide one or more of the advantages described herein. In some embodiments, the cannula insertion system 500 comprises a slider control mechanism 108. The slider control mechanism 108 can comprise a flexible beam portion 501 which can be configured to flex depending upon a position along a guide trail or channel 505 of a hollow tubular portion 103. In some embodiments, the slider control mechanism 108 comprises a substantially nonflexible or rigid beam portion 502 in the hollow tubular portion 103. In some embodiments, when the slider control mechanism 108 is in a proximal position, a needle portion coupled thereto is not distally extended.

In the proximal or loaded or first position shown in FIG. 6A, the flexible beam portion 501 is outwardly flexed due to interaction of the nonflexible beam portion 502 and a backward stopper portion 504 of a housing 402. The backward stopper portion 504 forces the slider control mechanism 108 inwardly towards the radial center of the device, causing the flexible beam portion 501 to flex upon interaction with an outer surface of the housing 402. In some embodiments, the flexible beam portion 501 comprises a protrusion 512 that interacts with the outer surface of the housing 402. In some embodiments, the user can slide the slider control mechanism 108 in a distal direction to a second position, allowing the nonflexible beam portion 502 to slide distally past the backward stopper protrusion 504, as shown in FIG. 6B. With the nonflexible beam portion 502 not interacting with the backward stopper protrusion 504, there is no longer an inward force on the slider control mechanism 108, and the flexible beam portion 501 is released from the flexed state.

In some embodiments, as the nonflexible beam portion 502 slides beyond the backward stopper protrusion 504, the slider control mechanism 108 is configured to make a clicking sound (e.g., upon the protrusion 512 falling into the trail 505), which may indicate to the user that the needle portion has advanced in body tissue such as the sclera. In some embodiments, the backward stopper protrusion 504 can be configured to interface with a distal portion 508 of the nonflexible beam portion 502 in order to inhibit or prevent the slider control mechanism 108 from moving backward in a proximal direction during use. In some embodiments the backward stopper protrusion 504 locks the slider control mechanism 108 with the shaft 404. In the locked state, any movement of the shaft 404 causes the slider mechanism and the needle portion 112 which is coupled to the slider control mechanism 108 to move in the same distal direction.

As illustrated in FIG. 6C, the activation mechanism 114 can be positioned in opening 510 of the tubular housing 103 of the device. In some embodiments, the outer edge of the activation mechanism 114 is flush with the outer surface of the tubular housing 103, which may inhibit or prevent accidental activating of the activation mechanism 114. In some embodiments, the outer surface of the activation mechanism 114 can be positioned slightly inward of or below the outer surface of the tubular housing 103, which can inhibit or prevent accidental activating of the activation mechanism 114. By inwardly depressing the activation mechanism 114, the deformed cantilever portion of the activation mechanism 114 is allowed to slide within the hollow tubular portion of the device 102, as shown in FIG. 6D.

Figure 7:
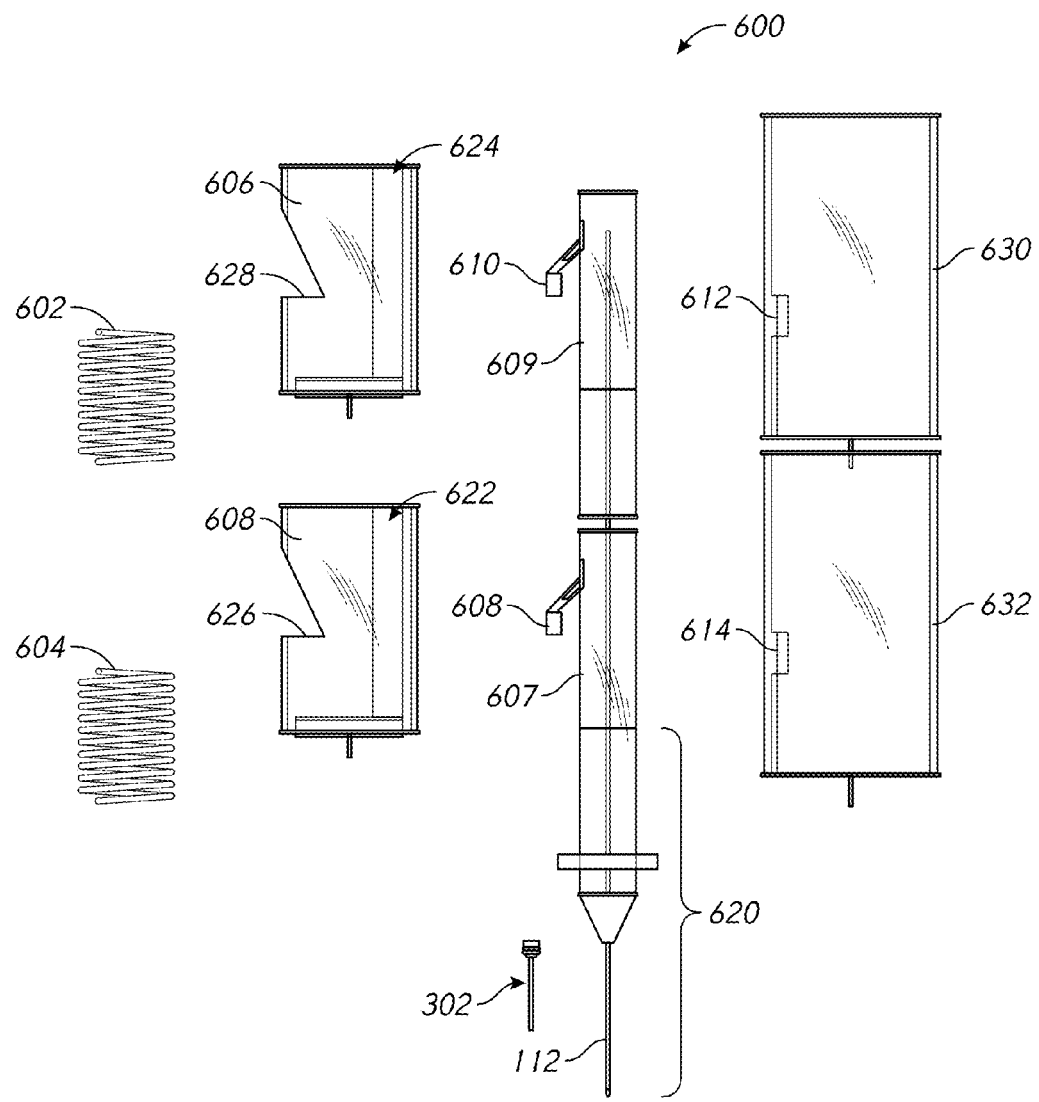
FIG. 7 is an exploded view of example components of an example cannula insertion system.
Figure 8:
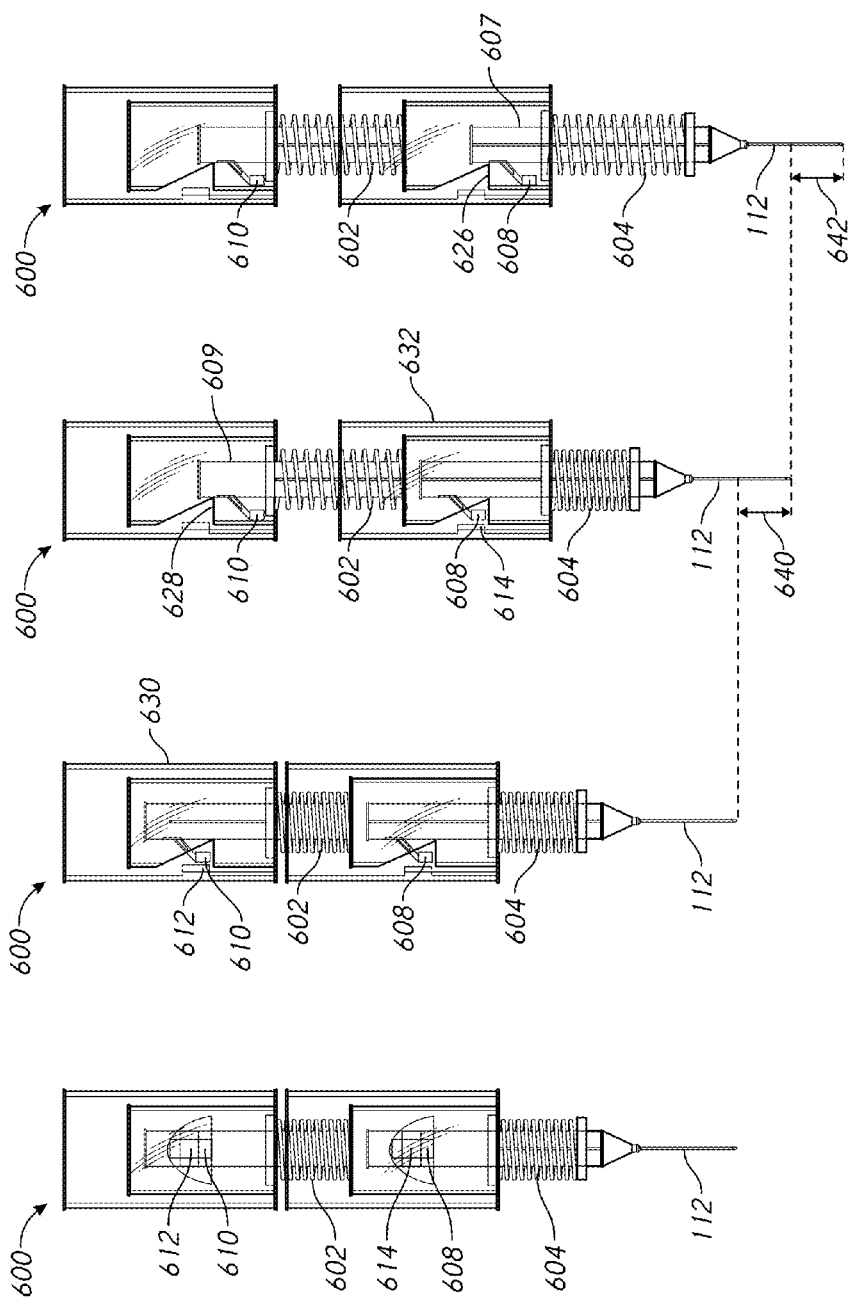
FIGS. 8A-8D illustrate example operations of an example cannula insertion system.

FIG. 7 is an exploded view of example components of an example cannula insertion system 600. In some embodiments, the cannula insertion system comprises a first spring 602 and a second spring 604 that can be used to implement a two-stage cannula insertion process. Along the lines described above with respect to the spring 106 and illustrated in FIGS. 5B and 5C, for example, and described in further detail with respect to FIGS. 8A-8D, the first spring 602 can be configured to advance the needle portion 112 slightly forward in a distal direction to allow the needle portion 112 to partially pierce body tissue such as the sclera, and, the second spring 604 can be configured to advance the needle portion 112 a longer distance in order to advance the needle portion 112 entirely through the body tissue. In some embodiments, the cannula insertion system comprises a first outer locking shell 606 comprising a first surface 628 and a first guide trail 624, a second outer locking shell 608 comprising a second surface 626 and a second guide trail 622, a first inner locking shaft 609 comprising an activation mechanism 610, a second inner locking shaft 607 comprising an activation mechanism 608, a trocar 620 including the needle portion 112, a cannula 302, a first sheath 630 comprising a first flexible activation button 612, and a second sheath 632 comprising a second flexible activation button 614. In some embodiments, the first and second springs, outer locking shells, inner locking shafts, and sheaths may be identical to each other or include at least one identical feature (e.g., size, shape, material, element, etc.).

FIGS. 8A-8D illustrate example operations of an example cannula insertion system 600. The system 600 may be used for form a one or two angle oblique sclerotomy, which may provide one or more of the advantages described herein. FIG. 8A is a front view and FIG. 8B is a side view of the cannula insertion system in an initial state. As illustrated in FIGS. 8A-8C, during a first stage, a user can activate the activation mechanism 610 by pressing the first flexible activation button 612 radially outward of the activation mechanism 610 to push the activation mechanism 610 radially inward and out of engagement with the surface 628, allowing the first inner locking shaft 609 to move distally and the first compressed spring 602 to expand, thereby forcing the needle portion 112 to move in a distal direction by a first distance 640. As illustrated in FIGS. 8C and 8D, during a second stage, a user can activate the activation mechanism 608 by pressing the first flexible activation button 614 radially outward of the activation mechanism 608 to push the activation mechanism 608 radially inward and out of engagement with the surface 626, allowing the second inner locking shaft 607 to move distally and the second compressed spring 604 to expand, thereby forcing the needle portion 112 to move in a distal direction by a second distance 642. The first distance 640 may be the same or different than the second distance 642.

An advantage that may be provided by the system 600 is that the advancement of the needle portion 112 is entirely automatic in that no distal movement by a user causes distal movement of the needle portion 112. A user need not exert any force on the needle portion 112 to pierce the body tissue. In comparison, in semi-automatic systems comprising a single spring, a user exerts some force on needle portion 112, for example by distally advancing a slider control mechanism 108, for the needle portion 112 pierce through body tissue during the first stage. In a completely automatic system, a user can advantageously exert a consistent force when inserting a cannula into body tissue. A user may expend less energy using a completely automatic system than a semi-automatic system. An automatic system can reduce the time for inserting a cannula into body tissue.

Figure 9:
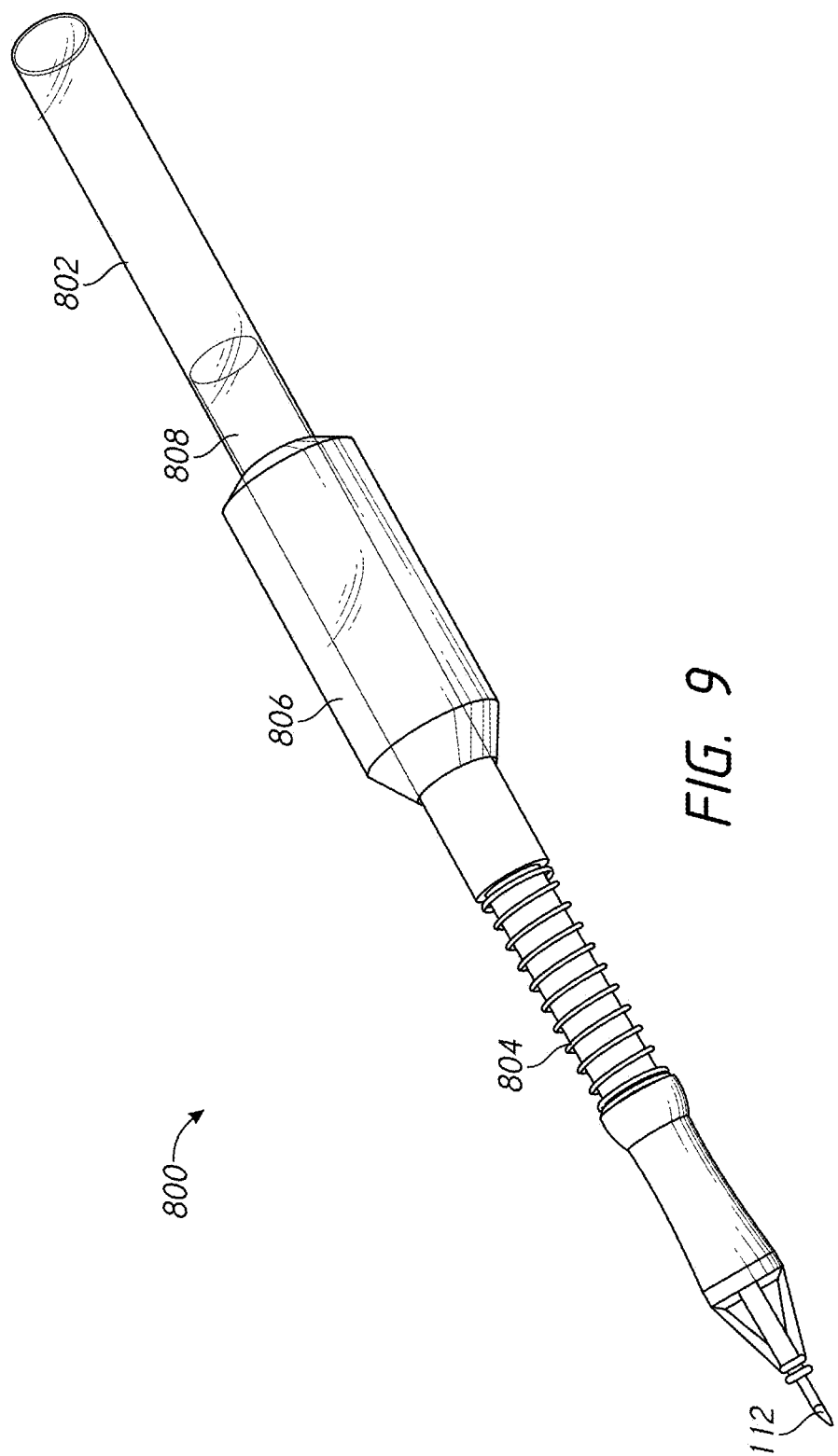
FIG. 9 is a perspective view of an example cannula insertion system.

FIG. 9 is a perspective view of an example cannula insertion system 800. In some embodiments, the cannula insertion system 800 is configured to insert a cannula into body tissue in one stage. In some embodiments, the cannula insertion system 800 comprises a compressed spring 804 coupled to an activation mechanism 806 and around an inner locking shaft 808, which is in an outer tube 802. An outer protection shell (e.g., around the spring 804) may be used. A user can activate the activation mechanism 806 to release the compressed spring 804 to exert force on the needle portion 112. The force exerted on the needle portion 112 drives the needle portion 112 into the body tissue.

Figure 10:
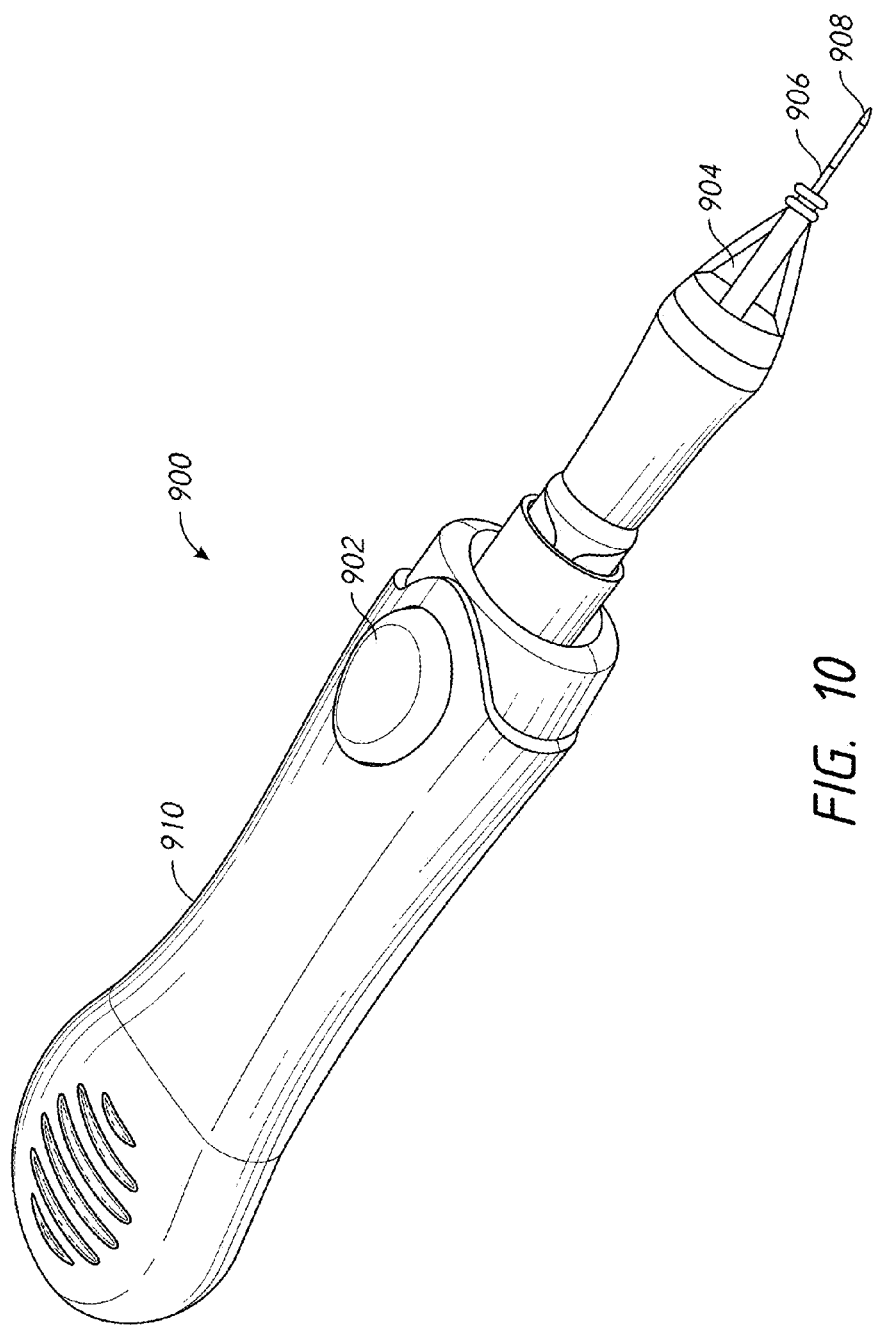
FIG. 10 is a perspective view an example cannula insertion system.

FIG. 10 is a perspective view an example cannula insertion system 900. In some embodiments, the cannula insertion system comprises a standard trocar 910 coupled to a lancing device 904, which includes a cannula 904 and a needle portion 908 (e.g., comprising a 25 gauge needle). In some embodiments, the cannula insertion system 900 comprises a button 902 that allows the user to release a compressed spring. By releasing the compressed spring, a force is exerted on the trocar 910, which drives the needle portion 908 and the cannula 906 of the lancing device 904 into body tissue.

Figure 11:
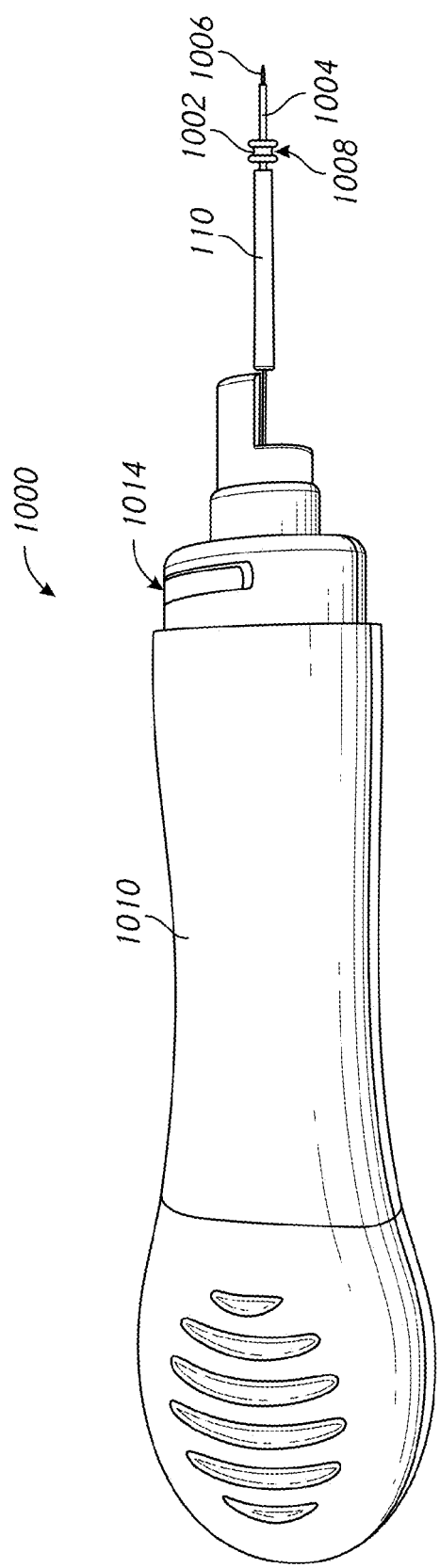
FIG. 11 is a perspective view an example cannula insertion system.

FIG. 11 is a perspective view an example cannula insertion system 1000. In some embodiments, the cannula insertion system 1000 comprises a standard trocar 1010 coupled to a slider portion 110, which includes a cannula 1008 and a needle portion 1006 (e.g., comprising a 25 gauge needle). In some embodiments, the needle portion 1006 is preloaded with the cannula 1008. In some embodiments, the cannula 1008 comprises a cannula body 1002 and a cannula tube 1004. In some embodiments, the cannula system 1000 comprises a button configured to release a compressed spring when activated by a user. Releasing the compressed spring causes a force to be exerted on the needle portion 1006 and the cannula 1008 as at least the needle portion 1006 and the cannula tube 1004 are inserted into body tissue.

Figure 12A:
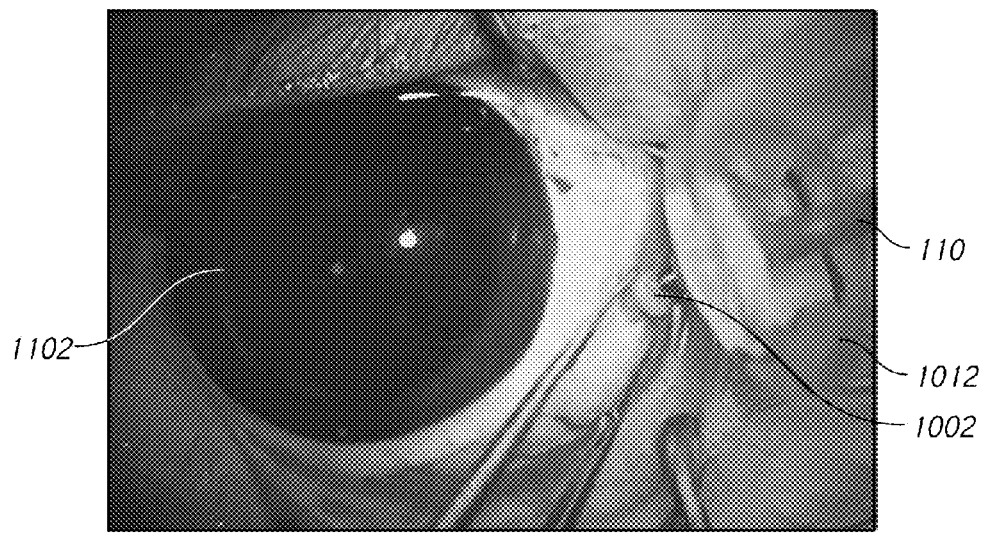
FIGS. 12A and 12B illustrate an example of inserting the example cannula insertion system of FIG. 11 in an eye.
Figure 12B:
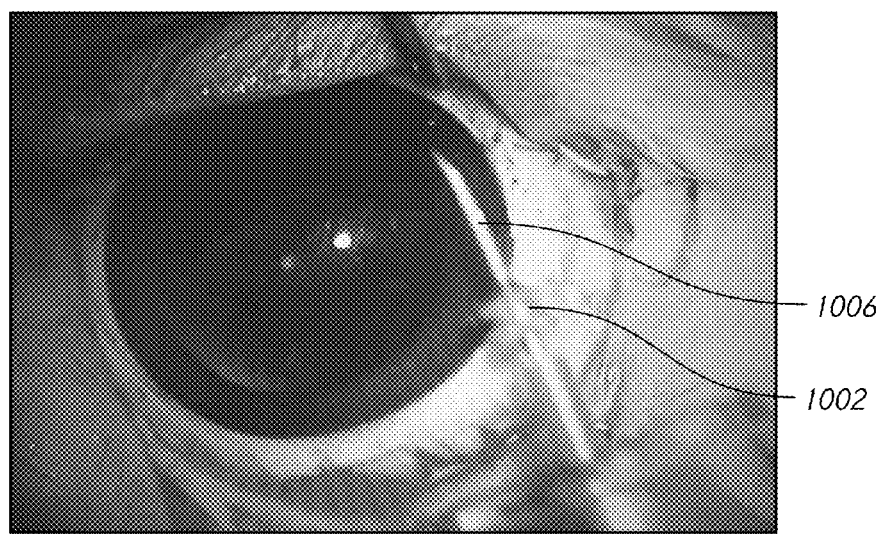

FIGS. 12A and 12B illustrate an example of inserting the cannula insertion system 1000 of FIG. 11 in an eye. The eye was a live rabbit eye, which is a suitable substitute representation of a human eye. In FIG. 12A, the slider mechanism 110 and the proximal portion of the cannula body 1002 are visible, and the needle portion 1006 and the cannula tube 1004 are in the eye. FIG. 12A also shows an optional protection tube 1012, which may be attached to the trocar 1006 and around the slider portion 110, for example using the channel 1014 shown in FIG. 11. FIG. 12B shows the extended needle 1006 after removal from the eye.

Figure 13D:
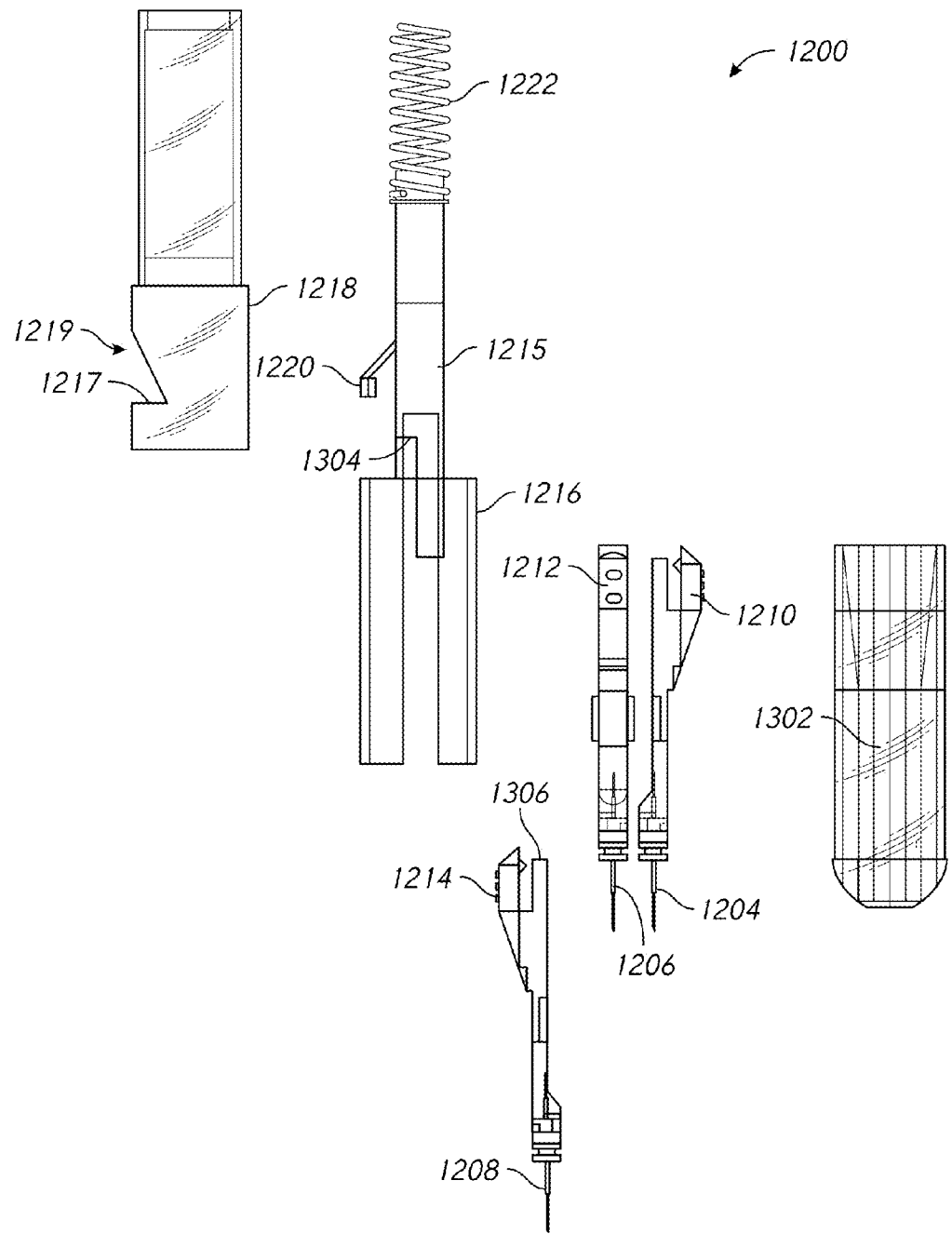
FIG. 13D is an exploded view of example components of the cannula insertion system of FIGS. 13A-13C.

FIGS. 13A-13C illustrate an example cannula insertion system 1200 at different stages. FIG. 13D is an exploded view of example components of the cannula insertion system 1200 of FIGS. 13A-13C. As shown in FIGS. 13A and 13D, for example, the cannula insertion system 1200 comprises a plurality of preloaded trocar-cannula pairs 1204, 1206, 1208. In some embodiments, the trocar-cannula pairs 1204, 1206, 1208 are coupled to a slide inserter 1210, 1212, 1214, respectively. In some embodiments, the cannula insertion system 1200 comprises a single slide inserter configured to be loaded with the trocar-cannula pairs 1204, 1206, 1208 when each trocar-cannula pair is about to be inserted in body tissue. In some embodiments, the cannula insertion system 1202 comprises two, three, four, five, or more preloaded trocar-cannula pairs each including an individual slide inserter. At least two and/or all of the trocar-cannula pairs may have a property (e.g., needle gauge, cannula gauge) that is the same as each other. At least two and/or all of the trocar-cannula pairs may have a property (e.g., needle gauge, cannula gauge) that is different from each other. The slide inserter 1210, 1212, 1214 may interlock with a cannula and needle portion as shown and described with respect to FIGS. 4A-4C, for example.

In some embodiments, the cannula insertion system 1200 comprises a housing 1218 having an opening 1219. The opening 1219 comprises an edge or surface 1217 configured to interface with a surface of a flexible trigger button 1220. Engagement between the flexible trigger button 1220 and the edge 1217 inhibits or prevents the interlocking shaft 1215 from being advanced forward due to the loaded, compressed spring 1222. In some embodiments, the cannula insertion system 1202 comprises a cover 1216 configured to protect the trocar-cannula pairs 1204, 1206, 1208.

In some embodiments, a user of the cannula insertion system 1200 rotates a guiding trail tube 1302 (e.g., through a window or aperture in the cover 1216) to place a desired one of the trocar-cannula pairs 1204, 1206, 1208 in a position for insertion into body tissue. For example, the user can position a trocar-cannula pair 1208 such that the slide inserter 1214 is aligned (e.g., circumferentially aligned) with the flexible trigger button 1220 (e.g., as illustrated in FIG. 12A).

In some embodiments, the cannula insertion system 1200 is configured to allow a user to longitudinally slide the slide inserter 1214 towards the distal end 1201 to allow the user to introduce the trocar needle partly into the sclera of a patient while creating a sclerotomy, as shown in FIG. 13B. In some embodiments, the slide inserter 1214 is configured to automatically and partially insert the trocar needle into the sclera by a spring mechanism (e.g., as described with respect to FIGS. 7-8D), motor, pneumatic drive, or other mechanism or other combination thereof, thereby avoiding the user sliding the slide inserter 1214. The system 1200 may be used for form a one or two angle oblique sclerotomy, which may provide one or more of the advantages described herein.

Figure 14A:
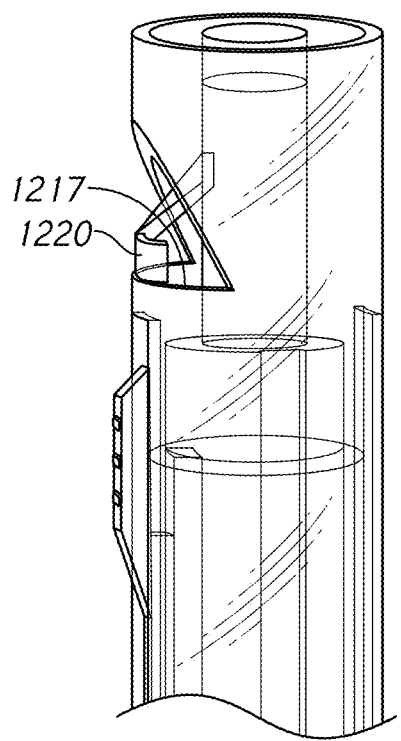
FIGS. 14A and 14B illustrate example operation of the cannula insertion system of FIGS. 13A-13C.
Figure 14B:
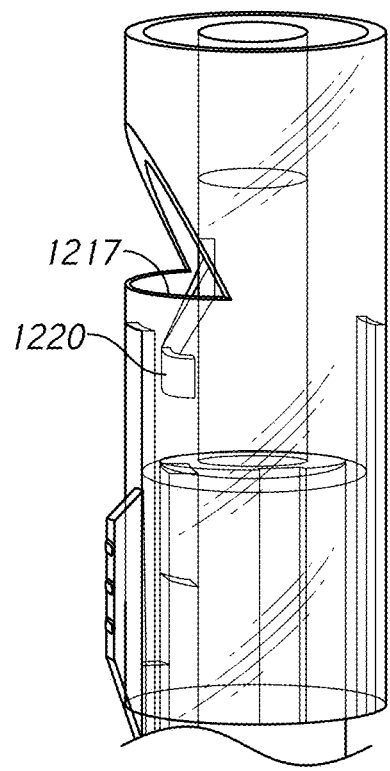

As shown in FIGS. 13C, 14A, and 14B, in some embodiments, the cannula insertion system 1200 is configured to allow the user to press and/or deform the flexible trigger button 1220 to allow the flexible trigger button 1220 to be disengaged with edge 1217 to release the compressed spring 1222. By disengaging the trigger button 1220 from the edge

1217, the spring 1222 is allowed to decompress and apply a force onto shaft 1215. By releasing the compressed spring 1222, the shaft 1215 can apply a longitudinal force on an edge 1306 (FIG. 13D) of the slide inserter 1214, which is aligned with an interface edge 1304 of the shaft 1215. By applying a longitudinal force on the slide inserter 1214, the trocar-cannula pair 1208 is forced further into the sclera of the patient. The trocar-cannula pair 1208 may be inserted through the sclera and the cannula may be implanted in the sclera.

During this two-stage insertion process, a user can first insert the trocar needle into the sclera at an oblique angle relative to the surface of an eye of a patient. In a second stage, the user can position the cannula insertion system 1200 at a substantially 90 degree angle relative to the surface of the eye before pressing and/or deforming the flexible trigger button 1220 such that a trocar-cannula pair is further inserted into the sclera by a distance 1224 by the longitudinal force exerted by the decompressing spring 1222.

To disengage the cannula insertion system 1200 from the inserted cannula, the cannula insertion system 1200 can be configured to allow the user to longitudinally slide the slide inserter 1214 towards the proximal end 1203. By moving the slide inserter 1214 towards the proximal end 1203, the trocar needle is withdrawn from the eye of the patient and from the cannula that is now implanted in the sclera of the eye. In some embodiments, the cannula insertion system 1202 can be configured to allow the user to rotate the protective cover 1216 to allow the user to insert a second trocar-cannula pair (e.g., the trocar cannula pair 1204 or the trocar cannula pair 1206) into the patient. To insert the second trocar-cannula pair into the patient, the user can repeat the foregoing process. The cannula insertion system 1200 can be used to insert multiple different cannulas into a patient.

In some embodiments, the cannula insertion system 1200 is configured to allow a user to compress the spring 1222 by longitudinally sliding the shaft 1215 toward the proximal end 1203 of the cannula insertion system 1200. The user can grasp the proximal end 1203 with one hand while using the other hand to longitudinally slide the shaft 1215 by grasping the cover 1216, which is coupled to the shaft 1215, near the distal end 1201 and moving the distal end 1201 towards the proximal end 1203 until the cantilever of the flexible trigger button flexes outwardly through the opening 1219 and the flexible trigger button 1220 engages the edge 1217.

Figures 15A, 15B, 15C:
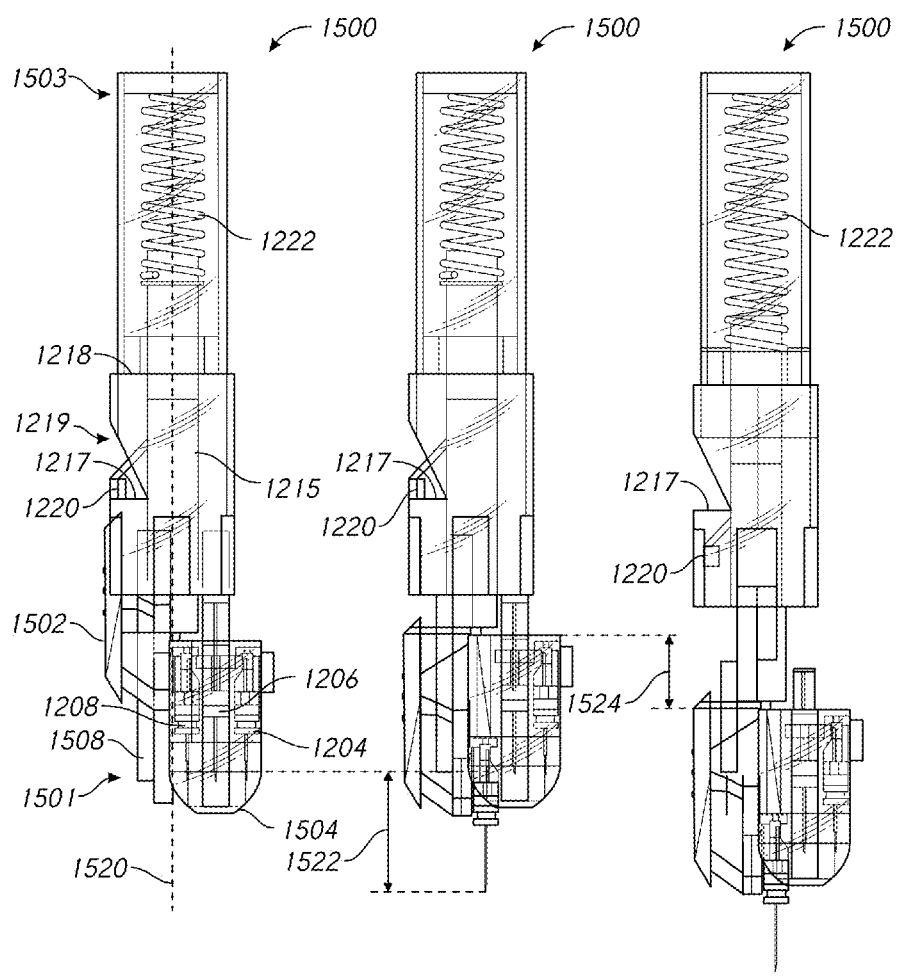
FIGS. 15A-15C illustrate an example cannula insertion system at different stages.
Figure 15D:
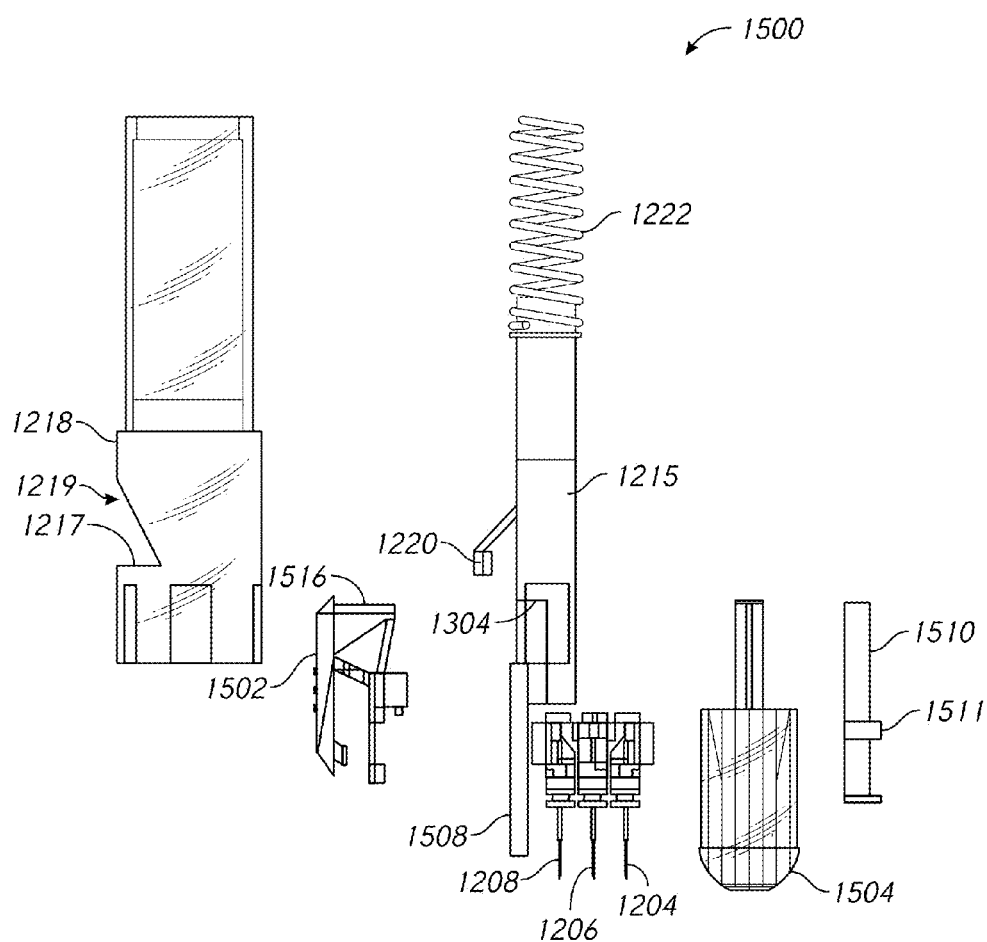
FIG. 15D is an exploded view of example components of the cannula insertion system of FIGS. 15A-15C.
Figure 15E:
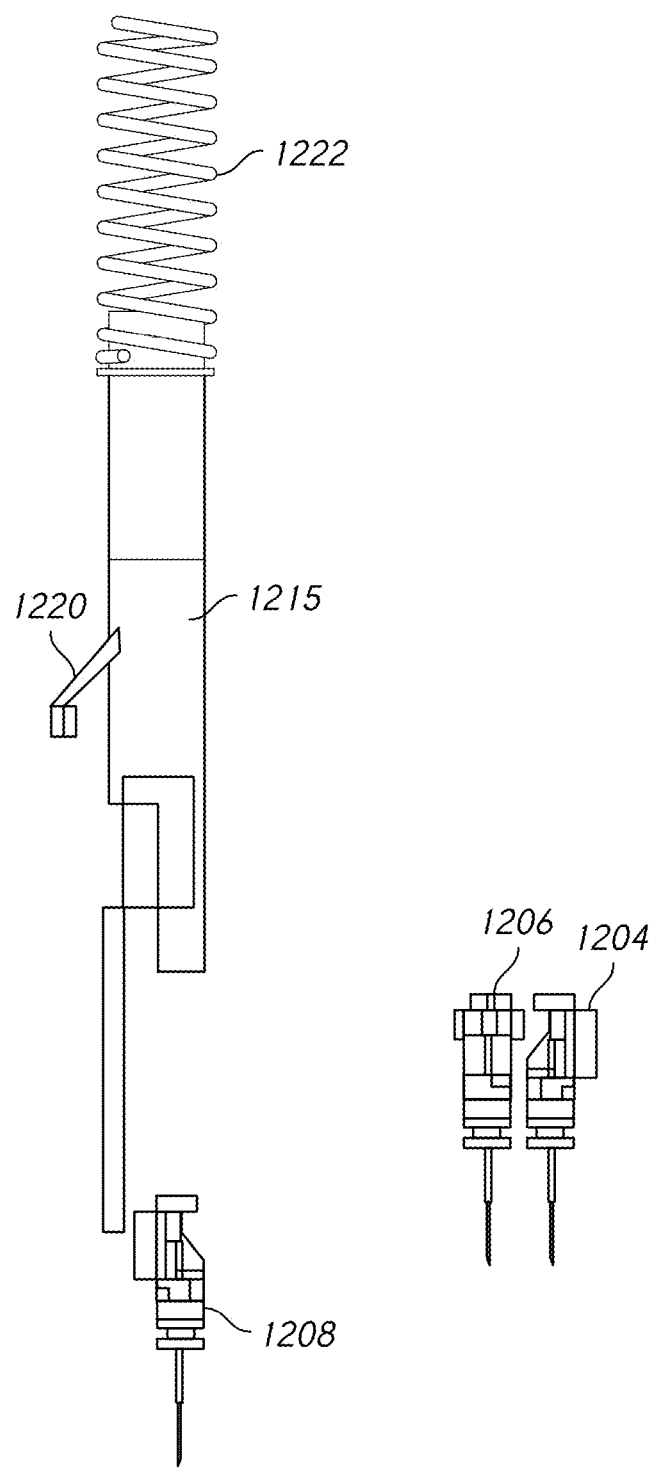
FIG. 15E is a further exploded view of example components of the cannula insertion system of FIGS. 15A-15C.

FIGS. 15A-15C illustrate an example cannula insertion system 1500 at different stages. FIG. 15D is an exploded view of example components of the cannula insertion system 1500 of FIGS. 15A-15C. FIG. 15E is a further exploded view of example components of the cannula insertion system 1500 of FIGS. 15A-15C.

As shown in FIGS. 15A and 15D, for example, the cannula insertion system 1500 comprises a revolver chamber 1504 configured to house a plurality of trocar-cannula pairs 1204, 1206, 1208. In some embodiments, the cannula insertion system 1500 includes a single or only one slide inserter 1502 configured to interact with and position any of the trocar-cannula pairs 1204, 1206, 1208, for example in contrast to the cannula insertion system 1200 in which each trocar-cannula pair was coupled to respective a slide inserter. In some embodiments, the revolver chamber 1504 can be configured to house a plurality of trocar-cannula pairs with each having a slide inserter, for example like the cannula insertion system 1200. In some embodiments, the revolver chamber 1504 can comprise two, three, four, five, or more trocar-cannula pairs for insertion into the eye of a patient. The revolver chamber 1504 may comprise trocar guide trails to longitudinally guide the trocar-cannula pairs upon application of force by the slide inserted 1502. At least two and/or all of the trocar-cannula pairs may have a property (e.g., needle gauge, cannula gauge) that is the same as each other. At least two and/or all of the trocar-cannula pairs may have a property (e.g., needle gauge, cannula gauge) that is different from each other.

In some embodiments, the cannula insertion system 1200 comprises a housing 1218 having an opening 1219. The opening 1219 comprises an edge or surface 1217 configured to interface with a surface of a flexible trigger button 1220. Engagement between the flexible trigger button 1220 and the edge 1217 inhibits or prevents the interlocking shaft 1215 from being advanced forward due to the loaded, compressed spring 1222.

In some embodiments, the revolver chamber 1504 is positioned or centered lateral to a center longitudinal axis 1520 of the cannula insertion system 1500. The revolver chamber 1504 can be positioned such that the desired trocar-cannula pair 1204, 1206, 1208 is placed substantially in the center longitudinal 1520 axis of the cannula insertion system 1500. In some embodiments, placement of the trocar-cannula pair in the center longitudinal axis 1520 allows the trocar-cannula pair to be aligned with the shaft 1215. The shaft 1215 is coupled to a guide rail 1508, which can guide the slide inserter 1502.

In some embodiments, the cannula insertion system 1500 is configured to allow a user to rotate the revolver chamber 1504 in order to place a selected trocar-cannula pair 1204, 1206, 1208 in a position for insertion into a patient. For example, the revolver chamber 1504 can be rotated such that the trocar-cannula pair 1208 is aligned with the slide inserter 1502 (e.g., as illustrated in FIG. 15A). In some embodiments, the cannula insertion system 1200 is configured to allow a user to longitudinally slide the slide inserter 1502 towards the distal end 1501 to allow the user to introduce the trocar needle partly into the sclera of a patient while creating a sclerotomy, as shown in FIG. 15B. FIG. 15E also shows the general longitudinal position of the trocar-cannula pairs 1204, 1206, 1208 after the trocar-cannula pair 1204 is moved due to movement of the slide inserter 1502. In some embodiments, the slide inserter 1502 is configured to automatically and partially insert the trocar needle into the sclera by a spring mechanism (e.g., as described with respect to FIGS. 7-8D), motor, pneumatic drive, or other mechanism or other combination thereof, thereby avoiding the user sliding the slide inserter 1502.

In some embodiments, the cannula insertion system 1500 is configured to allow the user to press and/or deform the flexible trigger button 1220 to allow the flexible trigger button 1220 to be disengaged with edge 1217 to release the compressed spring 1222, as shown in FIG. 15C. By disengaging the trigger button 1220 from the edge 1217, the spring 1222 is allowed to decompress and apply a force onto shaft 1215. The force on shaft 1215 can be applied to an edge 1516 (FIG. 15D) of the slide inserter 1502, which is aligned with an interface edge 1304 of the shaft 1215. By applying a longitudinal force towards the distal end 1501, the trocar-cannula pair 1208 is further driven into the sclera of the eye. The trocar-cannula pair 1208 may be inserted through the sclera and the cannula may be implanted in the sclera.

During this two-stage insertion process, a user can first insert the trocar needle into the sclera at an oblique angle relative to the surface of an eye of a patient. In a second stage, the user can position the cannula insertion system 1500 at a substantially 90 degree angle relative to the surface of the eye before pressing and/or deforming the flexible trigger button 1220 such that a trocar-cannula pair is further inserted into the sclera by a distance 1524 by the longitudinal force exerted by the decompressing spring 1222. The system 1500 may be used for form a one or two angle oblique sclerotomy, which may provide one or more of the advantages described herein.

In some embodiments, the cannula insertion system 1500 can be disengaged from the cannula that has been implanted in an eye of a patient by allowing the user to longitudinally slide the slide inserter 1502 toward the proximal end 1503. By sliding the slide inserter 1502 in a proximal direction, the trocar needle can be withdrawn from the implanted cannula. To insert a second cannula in the patient, the user to rotate the revolver chamber 1504 to position a second trocar-cannula pair (e.g., the trocar-cannula pair 1204 or the trocar-cannula pair 1206) at a location such that the second trocar-cannula pair is aligned with the slide inserter 1502. The user can then repeat the foregoing process in order to implant the second trocar-cannula pair. The cannula insertion system 1500 can be used to insert multiple different cannulas into a patient.

In some embodiments, the cannula insertion system 1500 is configured to allow the spring 1222 to be compressed when a user grasps the proximal end 1503 with one hand and longitudinally slides the shaft 1215 towards the proximal end 1503 by grasping the revolver chamber 1504, which is coupled to the shaft 1215, near the distal end 1501 and moving the distal end 1501 towards the proximal end 1503 until the cantilever of the flexible trigger button 1220 flexes outwardly through the opening 1219 and the flexible trigger button 1220 engages the edge 1217.

FIGS. 15F-15H illustrate an example cannula insertion system 1550 at different stages. FIGS. 15I-15K further illustrate example operations of the cannula insertion system 1550 of FIGS. 15F-15H. As shown in FIGS. 15D and 15F-15H, in some embodiments, the cannula insertion system 1550 optionally comprises one or more blockers 1510 for inhibiting or preventing the implantation of the non-aligned trocar-cannula pairs that are housed in the revolver chamber 1504. A cannula insertion system 1550 without a blocker 1510 may function as described above for the cannula insertion system 1500. The cannula insertion system 1550 is an example of a system comprising four trocar-cannula pairs, for example compared to the three trocar-cannula pairs of the cannula insertion system 1500. The components and operation of the cannula insertion system 1550 may otherwise be the same or substantially the same as the cannula insertion system 1500.

In some embodiments, the blocker 1510 is configured to lock the positions of the other trocar-cannula pairs such that the trocar-cannula pairs that are not in use are inhibited or prevented from sliding forward after the spring 1222 has been released from a compressed state. For example, the blocker 1510 may comprise a partially annular flange 1511 configured to interact with (e.g., mechanically impede movement of) a proximal portion of one, some, or all of the non-aligned trocar-cannula pairs.

Referring to FIGS. 15F and 15I, four trocar-cannula pairs 1204, 1206, 1208, 1209 are in the revolver chamber 1504 at an initial position. The trocar-cannula pair 1208 is aligned with the slide inserter 1502, which is radially outwardly deformed in a proximal position due to interaction of a flexible beam 1505 of the slide inserter 1502 with a more rigid or less flexible beam of the shaft 1215.

Referring to FIGS. 15G and 15J, the slide inserter 1502 has been longitudinally distally advanced. Advancement of the slide inserter 1502 distally advances the trocar-cannula pair 1208, which is free of the partially arcuate flange 1511 of the blocker 1510, by a distance 1522 and distal to the revolver chamber 1504. Advancement of the slide inserter 1502 does not distally advance the trocar-cannula pairs 1204, 1206, 1209 because the slide inserted 1502 does not interact with the trocar-cannula pairs 1204, 1206, 1209 and/or because the flange 1511 of the blocker 1510 inhibits or prevents advancement the trocar-cannula pairs 1204, 1206, 1209. After advancement, the slide inserter 1502 is no longer radially outwardly deformed since the flexible beam 1505 of the slide inserter 1502 is not interacting with a more rigid or less flexible beam of the shaft 1215. The flexible beam 1505 may flex radially inwardly and lock against a backward stopper 1515 of the slider 1215 to lock the slide inserter 1502 and trocar-cannula pair 1208 in the position shown in FIGS. 15G and 15J.

FIG. 15H shows the cannula insertion system 1550 after the flexible trigger button 1220 has been pressed or deformed radially inward to allow the flexible trigger button 1220 to disengage with edge 1217 to release the compressed spring 1222. By disengaging the trigger button 1220 from the edge 1217, the spring 1222 is allowed to decompress and apply a force onto shaft 1215. The force on shaft 1215 can be applied to an edge 1516 (FIG. 15D) of the slide inserter 1502, which is aligned with an interface edge 1304 of the shaft 1215. By applying a longitudinal force towards the distal end 1501, the trocar-cannula pair 1208 is driven a distance 1524 and further into the sclera of the eye. The system 1550 may be used for form a one or two angle oblique sclerotomy, which may provide one or more of the advantages described herein.

FIG. 15K shows the cannula insertion system 1550 in a partially retracted position, and for clarity omitting the revolver chamber 1504. The user first pulls and deforms the slide inserter 1502 radially outward so that the flexible beam 1505 can slide proximally past the backward stopper, and the user second proximally longitudinally retracts the slide inserter 1502. Retraction of the slide inserter 1502 also retracts the needle portion of the trocar-cannula pair 1208, leaving the cannula implanted in the sclera. The slide inserter may comprise a pivot point, weakened portion, and/or the like to promote deformation when desired. The next trocar-cannula pair can be aligned with the slide inserter 1502 and disengaged from the blocker 1510, and the foregoing process can be repeated.

FIG. 16 juxtaposes the cannula insertion system 1500 of FIGS. 15A-15C and the cannula insertion system of FIG. 1. In some embodiments, the cannula insertion system 1500 comprising a revolver chamber 1504 comprises similar dimensions and/or components as the example cannula insertion system 102, which does not comprise a revolver chamber, for example because the cannula insertion system 102 is configured to position a single cannula rather than a plurality of cannulas.

Figure 17E:
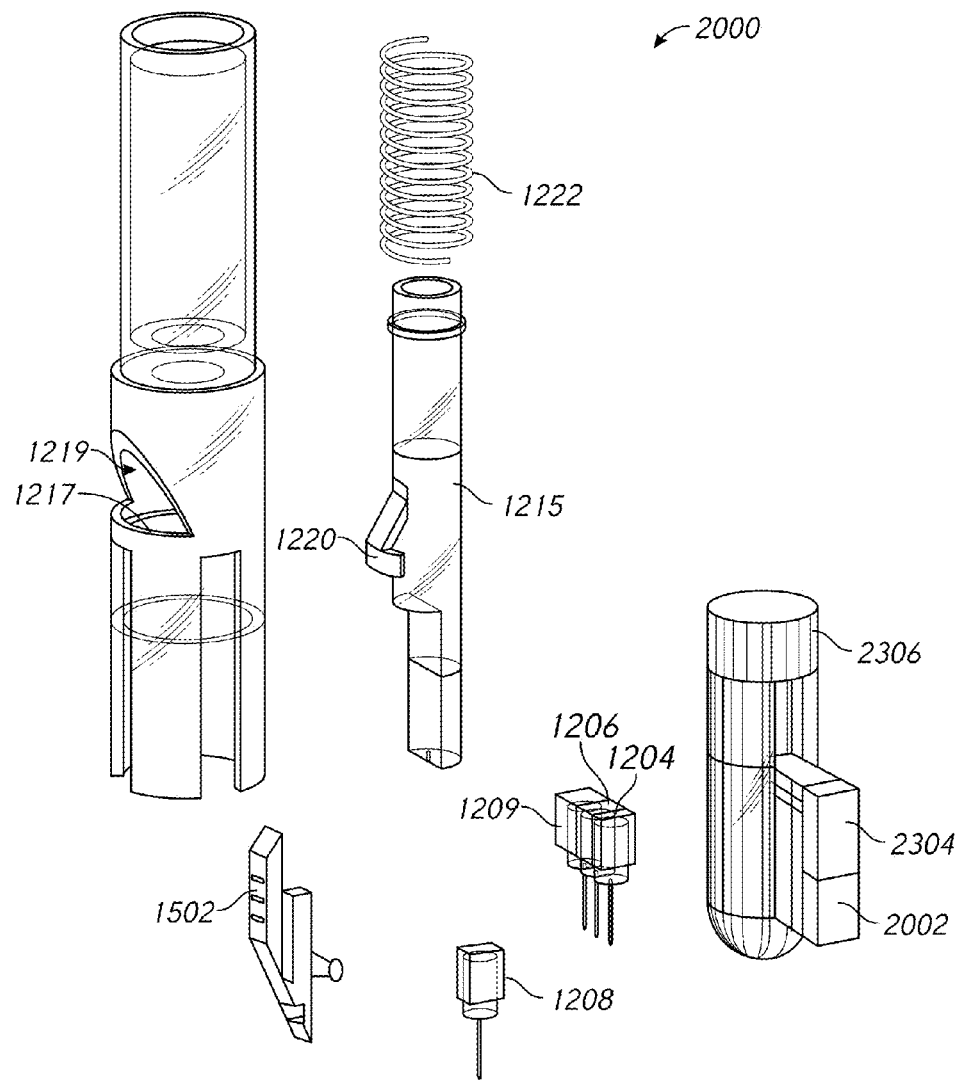
FIG. 17E is an exploded view of example components of the cannula insertion system of FIGS. 17A-17D.
Figure 17F:
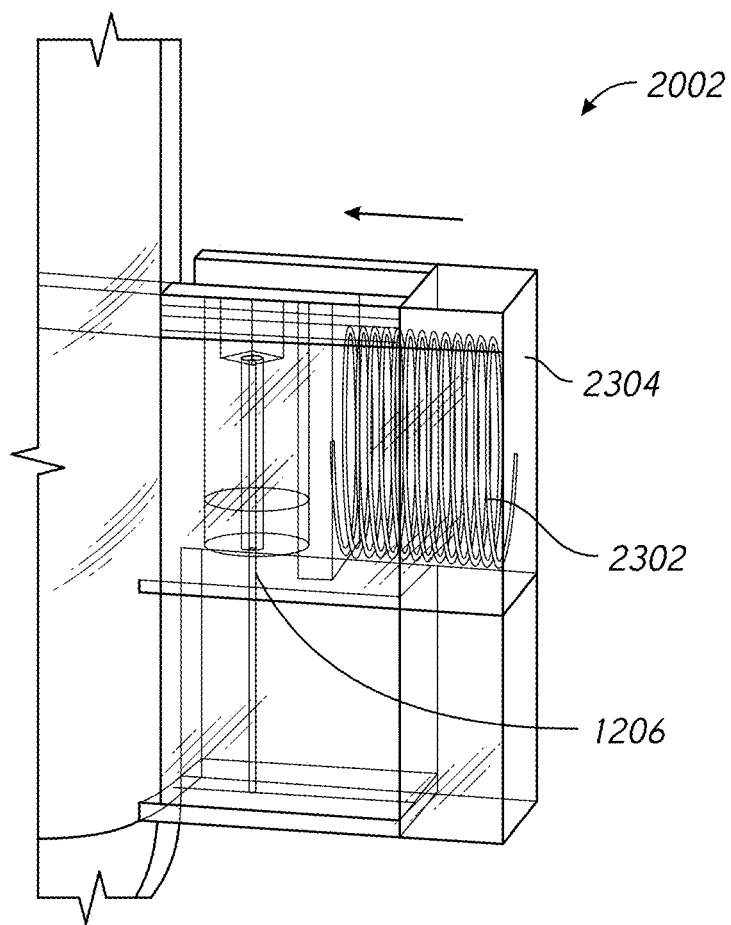
FIG. 17F is a magnified view of an example component of the cannula insertion system of FIGS. 17A-17D.

FIGS. 17A-17D illustrate an example cannula insertion system 2000. FIG. 17E is an exploded view of example components of the cannula insertion 2000 system of FIGS. 17A-17D. FIGS. 17A and 17B are side views and FIGS. 17C and 17D are front views. FIG. 17A shows the cannula insertion 2000 system in a first configuration, FIGS. 17B and 17C show the cannula insertion 2000 system in a second configuration, and FIG. 17D shows the cannula insertion 2000 system in a third configuration. FIG. 17F is a magnified view of an example component 2010 of the cannula insertion 2000 system of FIGS. 17A-17D.

The cannula insertion system 2000 comprises a side cartridge 2002 configured to house a plurality of trocar-cannula pairs 1204, 1206, 1208, 1209. In contrast to the guiding trail tube 1302 and the revolver chamber 1504, for example, which can be rotated to position a trocar-cannula pair for insertion, the side cartridge 2002 can transversely advance a trocar-cannula pair into position for insertion. In some embodiments, the cannula insertion system 2000 comprises a single slide inserter 1502 for implanting the plurality of trocar-cannula pairs housed in the side cartridge 2002, for example as described with respect to the cannula insertion systems 1500, 1550. In some embodiments, the cannula insertion system 2000 can comprise a plurality of slide inserters, one for implanting each of the plurality of trocar-cannula pairs housed in the side cartridge 2002, for example as described with respect to the cannula insertion system 1200. The trocar-cannula pairs 1204, 1206, 1208, 1209 can comprise a substantially rectangular or square or other shape configuration for positioning in the side cartridge 2002 and for loading the trocar-cannula pairs into the cannula insertion system 2000 for implantation into a patient. In some embodiments, the side cartridge 2002 is configured to house two, three, four, five, or more trocar-cannula pairs for insertion into the eye of a patient. At least two and/or all of the trocar-cannula pairs may have a property (e.g., needle gauge, cannula gauge) that is the same as each other. At least two and/or all of the trocar-cannula pairs may have a property (e.g., needle gauge, cannula gauge) that is different from each other.

In some embodiments, the cannula insertion system 2000 comprises a side cartridge 2002 that is proximate to the distal end 2001 of the cannula insertion system 2000. Referring to FIG. 17F, in some embodiments, the side cartridge 2002 comprises a button or surface 2304 that is coupled to a spring 2302. The side cartridge 2002 can be configured to allow the user to press the button 2304 in order to apply a force on spring 2302 such that a force is applied on the trocar-cannula pairs housed in the side cartridge 2002. The force on the trocar-cannula pairs is configured to horizontally, or transversely with respect to the longitudinal axis of the cannula insertion system 2000, slide at least one of the trocar-cannula pairs into a longitudinal center of the cannula insertion system 2000 to position that trocar-cannula pair to be implanted in a patient.

In some embodiments, the cannula insertion system 2000 is configured to allow a user to longitudinally advance the slide inserter 1502 towards the distal end 2001. By longitudinally advancing the slide inserter 1502 in the distal direction, the needle portion of the trocar-cannula pair 1208 can be initially inserted into the sclera of an eye of a patient. In some embodiments, the cannula insertion system 2000 is configured to allow the user to press and/or deform the flexible trigger button 1220 radially inward to disengage the flexible trigger button 1220 from the edge 1217. Disengagement of the flexible trigger button 1220 from the edge 1217 allows the spring 1222 to decompress and apply a force on the shaft 1215. The force applied on the shaft 1215 causes the shaft 1215 to apply a force on the slide inserter 1502, which causes the trocar-cannula pair 1208 to be inserted further into the sclera of an eye of a patient. The trocar-cannula pair 1208 may be inserted through the sclera and the cannula may be implanted in the sclera.

The user can position the cannula insertion system 2000 at an angle relative to the surface of the eye of the patient during the first stage illustrated from FIG. 17A to FIG. 17B, which includes inserting the trocar needle into the sclera using the slide inserter 1216. The user can position the cannula insertion system 2000 at substantially a 90 degree angle relative to the surface of the eye of the patient during the second stage illustrated from FIG. 17C to FIG. 17D, which includes inserting the trocar needle into the sclera by pressing and/or deforming the flexible trigger button 1220. The system 2000 may be used for form a one or two angle oblique sclerotomy, which may provide one or more of the advantages described herein.

To disengage the cannula insertion system 2000 from the implanted cannula, the cannula insertion system 2000 can be configured to allow the user to longitudinally slide the slide inserter 1502 towards the proximal end 2003. By retracting the slide inserter 1502 proximally, the needle portion of the trocar-cannula pair 1208 can be withdrawn from the implanted cannula. In some embodiments, the cannula insertion system 2000 is configured to allow the user to press the button 2304 to allow a second trocar-cannula pair to be horizontally moved into the cannula insertion system 2000 such that the second trocar-cannula pair can be placed in position for insertion into the eye using the foregoing process.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include, with or without user input or prompting, whether these features, elements and/or steps are included or are to be performed in any particular embodiment. The headings used herein are for the convenience of the reader only and are not meant to limit the scope of the inventions or claims.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. For example, actions such as "advancing a slide inserter" include "instructing advancement of a slide inserter." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 45°" includes "45°." Phrases preceded by a term such as "substantially" include the recited phrase and should be interpreted based on the circumstances (e.g., as much as reasonably possible under the circumstances). For example, "substantially nonflexible" includes "nonflexible."

What is claimed is:

1. A two-stage cannula insertion system comprising:
   a housing;
   a control mechanism slidably movable relative to the housing;
   a spring;
   an activation mechanism coupled to the spring;
   a shaft coupled to the spring, the shaft releasably engagable with the control mechanism, the control mechanism configured to move independently of the shaft when the shaft is disengaged with the control mechanism; and
   a trocar-cannula pair comprising a needle portion and a cannula and coupled to the control mechanism, the control mechanism is configured to advance the trocar-cannula pair during a first stage.

2. The system of claim 1, wherein the activation mechanism is configured to advance the trocar-cannula pair during a second stage.

3. The system of claim 1, further comprising a mechanical assembly housing a plurality of trocar-cannula pairs including the trocar-cannula pair, the mechanical assembly configured to disengage the needle portion from the control mechanism after the first stage, the mechanical assembly configured to couple a second trocar-cannula pair with the control mechanism.

4. The system of claim 3, wherein the mechanical assembly comprises a rotatable guiding trail tube having a longitudinal axis aligned with a longitudinal axis of the cannula insertion system.

5. The system of claim 3, wherein the mechanical assembly comprises a rotatable revolver chamber having a longitudinal axis radially offset from a longitudinal axis of the cannula insertion system.

6. The system of claim 3, wherein the mechanical assembly comprises a cartridge configured to horizontally advance the second trocar-cannula pair transverse to a longitudinal axis of the cannula insertion system.

7. A two-stage cannula insertion system for use in ophthalmic surgery, the system comprising:
   a mechanical assembly housing a plurality of trocar-cannula pairs including the trocar-cannula pair;
   a first stage insertion mechanism configured to insert the trocar-cannula pair partially into ocular tissue at a first angle, the trocar-cannula pair comprising a needle portion and a cannula; and
   a second stage insertion mechanism configured to insert the trocar-cannula pair through the ocular tissue at a second angle and to implant the cannula in the ocular tissue,
   the needle portion removable while maintaining the cannula in the ocular tissue.

8. The system of claim 7, wherein the first stage insertion mechanism is configured to releasably engage at least one of the plurality of trocar-cannula pairs housed in the mechanical assembly.

9. The system of claim 7, wherein at least one of the first stage insertion mechanism and the second stage insertion mechanism is configured to be automatically activated by a user engaging a button.

* * * * *